(12) United States Patent
Netemeyer et al.

(10) Patent No.: US 10,239,040 B2
(45) Date of Patent: Mar. 26, 2019

(54) FLOW REACTOR VESSELS AND REACTOR SYSTEMS

(71) Applicant: Chevron Phillips Chemical Company LP, The Woodlands, TX (US)

(72) Inventors: Eric J. Netemeyer, Kingwood, TX (US); Michael S. Matson, Bartlesville, OK (US); Greg L. Thomas, Dewey, OK (US); Dale M. Solaas, Fritch, TX (US); Christopher R. Tully, Borger, TX (US); Joe E. Figard, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/667,671

(22) Filed: Aug. 3, 2017

(65) Prior Publication Data
US 2017/0326525 A1 Nov. 16, 2017

Related U.S. Application Data

(62) Division of application No. 13/758,118, filed on Feb. 4, 2013, now abandoned.

(51) Int. Cl.
*B01J 19/24* (2006.01)
*B01J 19/12* (2006.01)
*B01J 19/00* (2006.01)
*C07C 319/04* (2006.01)
*C07C 319/18* (2006.01)
(Continued)

(52) U.S. Cl.
CPC ......... *B01J 19/2415* (2013.01); *B01J 19/006* (2013.01); *B01J 19/0073* (2013.01); *B01J 19/12* (2013.01); *B01J 19/123* (2013.01); *B01J 19/2405* (2013.01); *C07C 319/02* (2013.01); *C07C 319/04* (2013.01); *C07C 319/16* (2013.01); *C07C 319/18* (2013.01); *B01J 2219/00162* (2013.01); *B01J 2219/00511* (2013.01); *B01J 2219/0883* (2013.01); *B01J 2219/0884* (2013.01); *B01J 2219/0888* (2013.01); *B01J 2219/185* (2013.01)

(58) Field of Classification Search
None
See application file for complete search history.

(56) References Cited

U.S. PATENT DOCUMENTS

| 1,969,655 | A | 8/1934 | Mailey |
| 2,034,184 | A | 3/1936 | Hartman |

(Continued)

FOREIGN PATENT DOCUMENTS

| EP | 0 060 754 | 9/1982 |
| EP | 0 648 711 | 4/1995 |

(Continued)

OTHER PUBLICATIONS

International Search Report and Written Opinion of the International Search Authority in International Application No. PCT/US2014/014442 dated Jun. 18, 2014, 12 pages.

*Primary Examiner* — Kishor Mayekar
(74) *Attorney, Agent, or Firm* — Merchant & Gould PC

(57) ABSTRACT

The present invention discloses high pressure flow reactor vessels and associated systems. Also disclosed are processes for producing thiol compounds and sulfide compounds utilizing these flow reactor vessels.

20 Claims, 5 Drawing Sheets

(51) Int. Cl.
*C07C 319/02* (2006.01)
*C07C 319/16* (2006.01)

(56) References Cited

U.S. PATENT DOCUMENTS

| | | | |
|---|---|---|---|
| 3,019,267 A | | 1/1962 | Mahan et al. |
| 3,050,452 A | * | 8/1962 | Louthan ................ C07C 319/04 |
| | | | 204/157.76 |
| 3,248,315 A | * | 4/1966 | Warner ................ C07C 319/04 |
| | | | 204/157.76 |
| 3,257,302 A | | 6/1966 | Warner |
| 3,309,298 A | | 3/1967 | Yoshikazu et al. |
| 3,554,887 A | | 1/1971 | Feehs |
| 3,567,608 A | * | 3/1971 | Warner ................ C07C 319/04 |
| | | | 204/157.76 |
| 3,657,087 A | | 4/1972 | Scott |
| 4,140,604 A | | 2/1979 | Dimmig |
| 4,233,128 A | * | 11/1980 | Ollivier ................ C07C 319/04 |
| | | | 204/157.76 |
| 4,897,246 A | | 1/1990 | Peterson |
| 4,956,064 A | | 9/1990 | Evers et al. |
| 5,037,618 A | | 8/1991 | Hager |
| 5,093,086 A | | 3/1992 | Grossman et al. |
| 5,116,582 A | | 5/1992 | Cooper et al. |
| 5,247,178 A | | 9/1993 | Ury et al. |
| 5,372,781 A | | 12/1994 | Hallett et al. |
| 5,433,831 A | | 7/1995 | Kampmann et al. |
| 5,675,153 A | | 10/1997 | Snowball |
| 5,997,812 A | | 12/1999 | Burnham et al. |
| 6,171,558 B1 | | 1/2001 | Simpson |
| 6,238,628 B1 | | 5/2001 | Matsutani |
| 6,315,963 B1 | | 11/2001 | Speer |
| 6,503,464 B1 | | 1/2003 | Miki et al. |
| 6,589,489 B2 | | 7/2003 | Morrow et al. |
| 7,651,660 B2 | | 1/2010 | Kaiser et al. |
| 7,695,675 B2 | | 4/2010 | Kaiser et al. |
| 7,989,655 B2 | | 8/2011 | Refvik et al. |
| 8,080,165 B2 | | 12/2011 | Forney |
| 8,475,725 B1 | * | 7/2013 | Antipenko ............... C02F 1/325 |
| | | | 210/748.01 |
| 2003/0071224 A1 | | 4/2003 | Hallett et al. |
| 2004/0126273 A1 | | 7/2004 | Forney et al. |
| 2004/0249217 A1 | | 12/2004 | Agarwal et al. |
| 2005/0197391 A1 | | 9/2005 | Refvik et al. |
| 2006/0076506 A1 | | 4/2006 | Duthie, Jr. |
| 2009/0084734 A1 | | 4/2009 | Yencho |
| 2009/0155136 A1 | * | 6/2009 | Cooper ................ A61L 2/0011 |
| | | | 422/186.3 |
| 2012/0035291 A1 | | 2/2012 | Matson et al. |
| 2012/0051977 A1 | * | 3/2012 | Boodaghians .......... C02F 1/325 |
| | | | 422/117 |
| 2014/0131618 A1 | | 5/2014 | Matson |

FOREIGN PATENT DOCUMENTS

| | | |
|---|---|---|
| EP | 0 967 202 | 12/1999 |
| FR | 2 430 417 | 2/1980 |
| FR | 2 700 714 | 7/1994 |
| WO | WO 02/081080 | 10/2002 |

* cited by examiner

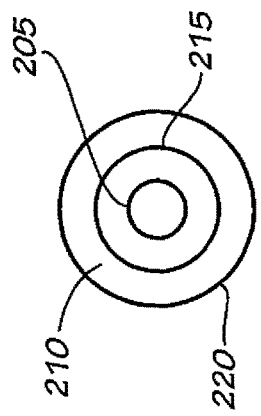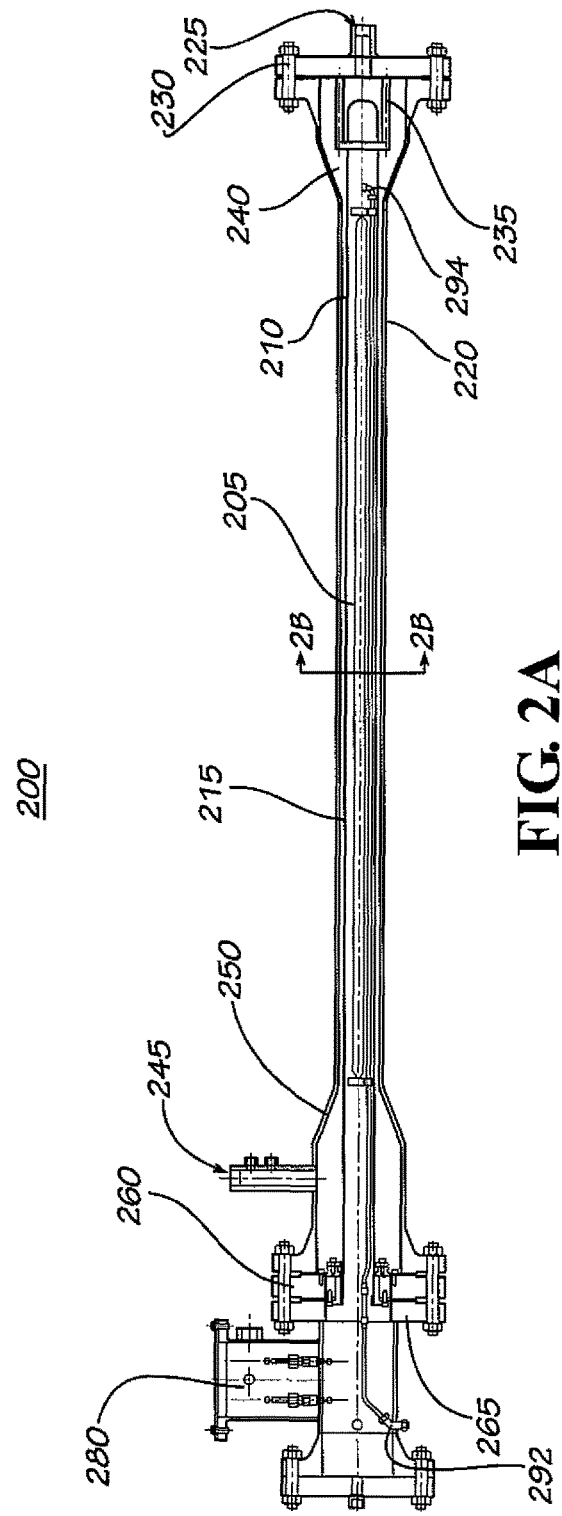

FLOW REACTOR VESSELS AND REACTOR SYSTEMS

This application is a divisional application of U.S. patent application Ser. No. 13/758,118, filed on Feb. 4, 2013, now abandoned, the disclosure of which is incorporated herein by reference in its entirety.

BACKGROUND OF THE INVENTION

The present invention relates generally to flow reactor vessels, and the use of these reactor vessels to conduct reactions to produce thiol compounds and sulfide compounds.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Various flow reactor vessels are disclosed herein. In one embodiment, a flow reactor vessel can comprise (a) a reaction chamber comprising a reactor wall, an inlet for a fluid, and an outlet; (b) a tube positioned within the reaction chamber, a flow path for the fluid including a region between an outer surface of the tube and an inner surface of the reactor wall; and (c) an electromagnetic radiation source enclosed within the tube, the electromagnetic radiation source configured to deliver radiation into the fluid in the flow path. In this flow reactor vessel, the average linear distance between the outer surface of the tube and the inner surface of the reactor wall can be configured, in some embodiments, to be less than 15 cm and/or a maximum of 1250 times the electromagnetic radiation penetration depth into the fluid in the flow path.

Embodiments of this invention also are directed to flow reactor systems containing two or more flow reactor vessels, configured in series, or in parallel, as well as combinations thereof.

Processes for forming thiol compounds also are disclosed herein. Generally, these processes can comprise (i) introducing a fluid comprising $H_2S$ and a compound having a carbon-carbon double bond into the inlet and the flow path of a flow reactor vessel; (ii) exposing the fluid to electromagnetic radiation within the reaction chamber of the flow reactor vessel to form a thiol compound; and (iii) discharging a composition comprising the thiol compound from the reaction chamber via the outlet. The molar ratio of $H_2S$ to carbon-carbon double bonds of the compound having a carbon-carbon double bond typically can range from 5:1 to 500:1.

Additionally, processes for forming sulfide compounds are disclosed herein. Generally, these processes can comprise (i) introducing a fluid comprising a mercaptan compound and a compound having a carbon-carbon double bond into the inlet and the flow path of a flow reactor vessel; (ii) exposing the fluid to electromagnetic radiation within the reaction chamber of the flow reactor vessel to form a sulfide compound; and (iii) discharging a composition comprising the sulfide compound from the reaction chamber via the outlet. The molar ratio of SH of the mercaptan compound to carbon-carbon double bonds of the compound having a carbon-carbon double bond typically can range from 5:1 to 1:5.

Both the foregoing summary and the following detailed description provide examples and are explanatory only. Accordingly, the foregoing summary and the following detailed description should not be considered to be restrictive. Further, features or variations may be provided in addition to those set forth herein. For example, certain embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present invention. In the drawings:

FIG. 2A shows a partial longitudinal cross-sectional view of a flow reactor vessel in another embodiment of the present invention.

FIG. 2B shows a partial transverse cross-sectional view of the flow reactor vessel of FIG. 2A.

DEFINITIONS

Figure 1:
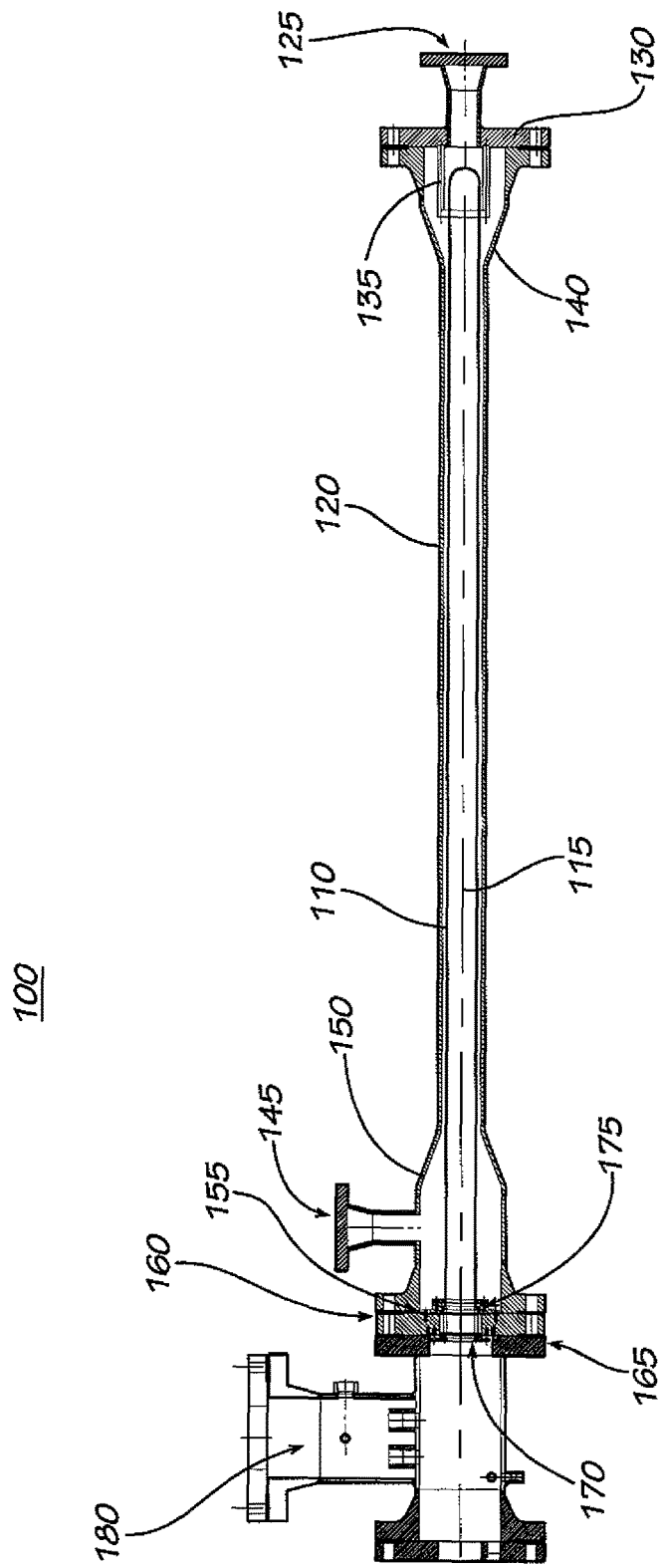
FIG. 1 shows a partial cross-sectional view of a flow reactor vessel in an embodiment of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified components or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. For example, a feedstock consisting essentially of component A can include impurities typically present in a commercially produced or commercially available sample of component A. When a claim includes different features and/or feature classes (for example, a method step, feedstock features, and/or product features, among other possibilities), the transitional terms comprising, consisting essentially of, and consisting of, apply only to the feature class to which it is utilized, and it is possible to have different transitional terms or phrases utilized with different features within a claim. For example, a method can consist of certain steps, but utilize a reaction mixture comprising recited components and other non-recited components. While devices and processes are described herein in terms of "comprising" various components or steps, the devices and processes can also "consist essentially of" or "consist of" the various components or steps, unless stated otherwise. For example, a flow reactor vessel consistent with embodiments of the present invention can comprise; alternatively, can consist essentially of; or alternatively, can consist of; a reaction chamber, a tube, and an electromagnetic radiation source.

The terms "a," "an," and "the" are intended to include plural alternatives, e.g., at least one. For instance, the disclosure of "a compound having a carbon-carbon double bond" is meant to encompass one, or mixtures or combinations of more than one compound, as well as compounds having two or more carbon-carbon double bonds, etc., unless otherwise specified.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

A chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbyl group" is used herein in accordance with the definition specified by IUPAC: a univalent group formed by removing a hydrogen atom from a hydrocarbon (i.e., containing only carbon and hydrogen). Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic, and/or linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane groups, cycloalkyl, cycloalkylene, cycloalkane groups, alkylaryl/arylalkyl, aralkylene, and aralkane groups, respectively, amongst other groups as members.

The compounds disclosed herein have at least one carbon-carbon double bond (e.g., compounds having one carbon-carbon double bond, two carbon-carbon double bonds, three carbon-carbon double bonds, etc.). These carbon-carbon double bonds (e.g., —C═C—), or olefinic double bonds, are non-aromatic double bonds, but the carbon-carbon double bonds can be located at any position (e.g., terminally or internally) in the compound, unless specified otherwise or the context requires otherwise.

An aliphatic compound is an acyclic or cyclic, saturated or unsaturated compound, excluding aromatic compounds. That is, an aliphatic compound is a non-aromatic organic compound. Aliphatic compounds, and therefore aliphatic groups, can contain organic functional group(s) and/or atom(s) other than carbon and hydrogen. An "aliphatic group" is a generalized group formed by removing one or more hydrogen atoms (as necessary for the particular group) from a carbon atom of an aliphatic compound.

The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic, and/or linear or branched, unless otherwise specified. Primary, secondary, or tertiary alkyl groups are derived by removal of a hydrogen atom from a primary, secondary, or tertiary carbon atom, respectively, of an alkane. The n-alkyl group is derived by removal of a hydrogen atom from a terminal carbon atom of a linear alkane. The groups RCH$_2$ (R≠H), R$_2$CH (R≠H), and R$_3$C (R≠H) are primary, secondary, and tertiary alkyl groups, respectively.

A cycloalkane is a saturated cyclic hydrocarbon, with or without side chains, for example, cyclobutane and methylcyclobutane. Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. A "cycloalkyl group" is a univalent group derived by removing a hydrogen atom from a ring carbon atom from a cycloalkane. For example, a 1-methylcyclopropyl group and a 2-methylcyclopropyl group are illustrated as follows:

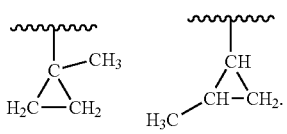

Similarly, a "cycloalkylene group" refers to a group derived by removing two hydrogen atoms from a cycloalkane, at least one of which is a ring carbon. Thus, a "cycloalkylene group" includes a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane.

The terms "contact product," "contacting," and the like, are used herein to describe compositions wherein the components are contacted together in any order, in any manner, and for any length of time. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a hydrocarbyl group having from 1 to 18 carbon atoms (i.e., a $C_1$-$C_{18}$ hydrocarbyl group), as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a hydrocarbyl group having 3 to 8 carbon atoms), and also including any combination of ranges between these two numbers (for example, a hydrocarbyl group having 1 to 4 carbon atoms and a hydrocarbyl group having 8 to 12 carbon atoms).

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

DETAILED DESCRIPTION OF THE INVENTION

The following detailed description refers to the accompanying drawings. Wherever possible, the same or similar reference numbers are used in the drawings and the following description to refer to the same or similar elements or features. While various embodiments of the invention are described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description and its exemplary embodiments do not limit the scope of the invention.

Flow Reactor Vessels

FIG. 1 illustrates an embodiment of a flow reactor vessel 100 consistent with the present invention. The flow reactor vessel 100 can include a reactor wall 120, with a tube 115 enclosing an electromagnetic radiation source (not shown) housed within the reactor wall 120 of the flow reactor vessel 100. The flow reactor vessel can contain an inlet 125 for a fluid and an outlet 145 as shown in FIG. 1, although it is contemplated the inlet and outlet locations can be reversed. As illustrated, the inlet 125 is generally parallel to the tube 115 (e.g., to minimize tube stress and/or vibration), while the outlet 145 is generally perpendicular to the tube 115, but other angles and orientations can be employed. Generally, the reactor wall 120 and other reactor surfaces can be constructed of any suitable metal material, such as carbon steel, stainless steel, and the like. The reactor wall 120 in sections of the flow reactor vessel that are not proximate to the inlet 125 and the outlet 145 can be generally cylindrical, although this is not a requirement.

Similarly, the tube 115 generally can be cylindrical in shape, but is not limited thereto. For instance, as an alternative to a circular cross-section, the tube 115 can have an elliptical or oval cross-section. The tube 115 can be constructed of any suitable material, the selection of which can depend upon the desired operating temperature, desired operating pressure, inertness to the fluids contained within the flow reactor vessel, and appropriateness for the particular electromagnetic radiation source employed, amongst other factors. Illustrative and non-limiting examples of materials that can be used to form the tube 115 can include, but are not limited to, quartz, Pyrex®, sapphire (e.g., man-made sapphire), and various plastics, such as polyamide, polycarbonate, etc. If the electromagnetic radiation source is an ultraviolet light, for instance, a material such as quartz would be preferable to materials such as plastics, which often can degrade in the presence of UV light or inhibit the penetration of UV light into the flow path. The use of a quartz tube 115 will be referred to throughout the remainder of this disclosure, although other alternative materials can be substituted in view of the factors provided herein (e.g., electromagnetic radiation sources other than UV light). The wall thickness of the tube (e.g., the quartz tube) can vary depending on several factors (e.g., pressure and flow rate considerations) and can be any thickness suitable for the tube diameter and material utilized. In an embodiment, the minimum wall thickness of the tube can be at least 1 mm, 2 mm, 2.5 mm, 3 mm, 3.5 mm, 4 mm, 4.5 mm, or 5 mm, while the maximum wall thickness of the tube can be 10 mm, 9 mm, 8 mm, 7.5 mm, 7 mm, 6.5 mm, 6 mm, 5.5 mm, 5 mm, 4.5 mm, or 4 mm. The wall thickness of the tube can range from any minimum wall thickness of the tube disclosed herein to any maximum wall thickness of the tube disclosed herein. Representative non-limiting ranges for the wall thickness of the tube (e.g., the quartz tube) include from 1 to 10 mm, from 2 to 10 mm, from 1 to 5 mm, from 2 to 5 mm, from 2.5 to 4.5 mm, and the like. Other ranges for the wall thickness of the tube are readily apparent from the present disclosure.

A flow area 110 (also referred to as a flow path) of the flow reactor vessel 100 is located in the region or space between the quartz tube 115 and the reactor wall 120. If the quartz tube 115 and the reactor wall 120 are generally cylindrical and concentric, then the flow area 110 includes the annular region between the outer surface of the quartz tube and the inner surface of the reactor wall. Fluid can enter the inlet 125 of the flow reactor vessel 100, proceed generally longitudinally in the flow area 110 between the quartz tube 115 and the reactor wall 120, and exit through the outlet 145.

The flow reactor vessel 100 can include a compression seal assembly for sealing and/or securing the quartz tube (and electromagnetic radiation source, such as a UV lamp) to the reaction chamber, and moreover, this compression seal assembly can be configured for operating pressures of at least 1.72 MPa. In some embodiments, the compression seal assembly, the tube, the reactor wall, and the flow reactor vessel in general (e.g., the reaction chamber), can be configured to operate at a minimum pressure of at least 1.72 MPa, at least 2.41 MPa, at least 2.76 MPa, at least 3.45 MPa, or at least 4.14 MPa, while in other embodiments, configured to operate at a maximum pressure of 13.79 MPa, 10.34 MPa, 6.89 MPa, 5.17 MPa, or 3.44 MPa. The reaction chamber can be configured to operate at a pressure in a range from any minimum pressure disclosed herein to any maximum pressure disclosed herein. For example, the flow reactor vessel and reaction chamber can be configured to operate at pressures in a range from 1.72 to 13.79 MPa, from 2.07 to 13.79 MPa, from 1.72 to 10.34 MPa, from 2.07 to 10.34 MPa, from 1.72 to 6.89 MPa, or from 2.07 to 5.17 MPa, and the like. Other pressure ranges for which the reaction chamber can be configured to operate are readily apparent from the present disclosure. In other embodiments, however, the flow reactor vessel 100 can be configured to operate at a maximum pressure of 3.44 MPa, 1.72 MPa, 1.38 MPa, 1.03 MPa, 0.69 MPa, 0.52 MPa, 0.34 MPa, while in other embodiments, configured to operate at a minimum pressure of 0.10 MPa, 0.14 MPa, 0.17 MPa, or 0.34 MPa. Accordingly, the flow reactor vessel and reaction chamber can be configured to operate at a pressure in a range from 0.1 to 3.44 MPa, from 0.14 to 1.38 MPa, from 0.14 to 1.03 MPa, from 0.14 to 0.69 MPa, from 0.14 to 0.52 MPa, or from 0.17 to 1.03 MPa. Other pressure ranges for which the reaction chamber can be configured to operate are readily apparent from the present disclosure.

This compression seal assembly in FIG. 1 can include one or more of the following parts, but is not limited only to these parts or their reasonable equivalents: support 155, spacer ring 175, securing flange 160, packing gland 170, and outer flange 165. The support 155 and the securing flange 160 can be used to secure the quartz tube 115 to the metal reaction chamber (both the support 155 and the securing flange 160 are typically a metal material). To provide cushioning and to prevent direct metal to quartz contact, the spacer ring 175 can be positioned between the support 155 and the quartz tube 115. The spacer ring can be any suitable flexible material, such as rubber or Teflon®, but is not limited thereto. For high pressure operation, the packing gland 170 can provide a high pressure seal for the quartz tube 115, and generally can be positioned between the outer quartz wall and the securing flange 160. The packing gland can be a multi-part flexible material, constructed of rubber or Teflon® or related materials, a commercially-available example of which is John Crane Part No. T02656. Outer flange 165, on the outlet side of the flow reactor vessel, can both secure the reaction chamber and provide secondary containment, in the event the quartz tube were to crack or break.

An electrical connection 180 can be included to provide suitable power to the electromagnetic radiation source (not shown) contained within the quartz tube 115. An inlet expansion section 140 and an outlet expansion section 150 can be provided, if desired, near the inlet 125 and the outlet 145, respectively. An inlet side reactor flange 130 also can be provided either near or at the reactor inlet 125.

At the terminating end of the quartz tube 115 and proximate the reactor inlet 125, a tube retainer 135 can be employed to stabilize the quartz tube. While one end of the quartz tube is sealed and secured to the reaction chamber, e.g., via the compression seal assembly, the other end, in some embodiments, is not clamped or bound. Due to the different thermal expansion and contraction properties of quartz and of the metals typically employed in the reactor, securing the quartz tube at both ends can lead to fatigue and/or breakage during start-up, shutdown, and/or continuous operation. The retainer 135 can permit relative movement (e.g., expansion or contraction) between the quartz tube 115 and the reactor wall 120, but generally can minimize or prevent wobble and/or deflection of the quartz tube during operation, for example, due to the contacting of the tube by the incoming flow of material thru the reactor inlet 125. Many retainer designs are possible, but one suitable design is a metal material with an inner coating or layer of a softer, flexible material (e.g., Gore Packing Material). In some embodiments, the retainer 135 is not in direct contact with the quartz tube 115 (e.g., fluid can flow between the retainer and the tube), while in other embodiments, at least a portion of the inner layer of the retainer can be in direct contact with the quartz tube. Other designs and locations for the retainer, configured to prolong the life of the tube and to permit relative expansion/contraction, are contemplated and encompassed herein.

The spatial orientation of the flow reactor vessel 100 in FIG. 1 is not particularly limited, however, in some embodiments, the flow reactor vessel is oriented vertically. In these embodiments, the flow reactor vessel can be positioned vertically such that the inlet 125 is the lowest point of the flow reactor vessel, i.e., the outlet 145 is at a higher altitude than the inlet 125.

Referring now to FIG. 2A, another flow reactor vessel 200 is illustrated. Similar to FIG. 1, the flow reactor vessel 200 of FIG. 2A can include a reactor wall 220, a quartz tube 215, a flow area or flow path 210 between the wall and the tube, an inlet 225, an outlet 245, an inlet side reactor flange 230, an outlet side reactor flange 265, a securing flange 260, an electrical connection 280, and a tube retainer 235, generally the same as described above in relation to FIG. 1.

An electromagnetic radiation source, such as a UV lamp 205, configured to deliver radiation into the fluid in the flow path 210 is enclosed within the quartz tube 215 as illustrated in FIG. 2A. The radiation source is not particularly limited, provided that it is capable of delivering at least one type of radiation, e.g., radio waves, microwaves, infrared radiation, visible light, ultraviolet radiation, X-rays, gamma rays, and the like, as well as combinations thereof, into the flow path. In one embodiment, for instance, the electromagnetic radiation source can be an ultraviolet light source capable of directing ultraviolet light at a wavelength in the 172 to 450 nm range, in the 185 to 380 nm range, in the 200 to 350 nm range, in the 245 to 300 nm range, in the 253 to 256 nm range, in the 265 to 266 nm range, or in the 296 to 298 nm range, into the fluid in the flow path. It should be understood while a particular ultraviolet wavelength range can be selected, the ultraviolet light source can produce wavelengths (which can be directed into the fluid flow path) in one or more (or even all) of these wavelength ranges, and also wavelengths outside of these wavelength ranges, as long as the ultraviolet light source produces at least one wavelength inside of at least one of the selected wavelength ranges.

An inert gas delivery system is shown in FIG. 2A, with a gas inlet 292 and a gas outlet 294, although it is contemplated the inlet and outlet locations can be reversed. The inert gas delivery system can provide an inert atmosphere (e.g., no air or oxygen) within the quartz tube 215 and around the UV lamp 205. Any suitable inert gas (or gasses) can be employed, such as nitrogen, argon, etc.

The UV lamp 205 often can be located within a cylindrical section of the flow reactor vessel 200, where the quartz tube 215 and the reactor wall 220 are generally concentric, although this is not a requirement. For example, the UV lamp can be located outside this concentric region and directed into the fluid flow path using a UV reflective surface. In a concentric arrangement, an inlet expansion section 240 and an outlet expansion section 250 can be employed in reaction chamber areas extending beyond the ends of the UV lamp 205. The concentric configuration in some non-limiting embodiments described herein is illustrated in FIG. 2B, which shows a transverse cross-sectional view of the flow reactor vessel of FIG. 2A. For clarity, the inert gas delivery system and any parts including and beyond the inlet expansion section 240 are omitted. FIG. 2B illustrates the location of the UV lamp 205 within the quartz tube 215, the concentricity of the quartz tube 215 and the reactor wall 220, and the flow area or flow path 210 being an annular region therebetween.

As disclosed herein, the average linear distance between the outer surface of the tube 215 and the inner surface of the reactor wall 220 can be configured to be a maximum of 1250 times the electromagnetic radiation penetration depth into the fluid in the flow area 210. The average linear distance is used herein to account for embodiments where the tube and reactor wall cross-sections are not circular, embodiments where the tube is offset from the center of the reaction chamber, etc. For embodiments in which the tube and reactor wall have circular cross-sections, and the tube is centered within the reactor (see FIG. 2B), the average linear distance can be determined by subtracting the radius of the outer surface of the tube (O.D.) from the radius of the inner surface of the reactor wall (I.D.). Additionally, these average linear distances, as well as other dimensional relationships provided herein below, are limited to areas where the electromagnetic source (e.g., the UV lamp) is positioned and is delivering radiation into the fluid in the flow path. For example, these dimensional relationships apply in longitudinal areas of the flow reactor vessel where the UV lamp 205 in FIG. 2A is located, and not to the inlet expansion section 240, the outlet expansion section 250, etc., and other longitudinal areas beyond the ends of the UV lamp 205.

In some embodiments, the average linear distance between the outer surface of the quartz tube 215 and the inner surface of the reactor wall 220 can be configured to be less than or equal to 1250 times, 1000 times, 750 times, 500 times, 450 times, 400 times, 350 times, 300 times, 250 times, 200 times, 150 times, 100 times, 75 times, 50 times, 40 times, 30 times, 25 times, or 15 times the electromagnetic radiation penetration depth into the fluid in the flow path. In other embodiments, the average linear distance between the outer surface of the quartz tube 215 and the inner surface of the reactor wall 220 can be configured to be greater than or equal to 1 times, 1.1 times, 1.25 times, 1.5 times, 1.75 times, 2 times, 2.5 times, 3 times, 3.5 times, 4 times, 5 times, 10 times, 25 times, 50 times, or 75 times the electromagnetic radiation penetration depth into the fluid in the flow path. Exemplary ranges for this average linear distance can include, but are not limited to, from 1 to 1000 times, from 10 to 500 times, from 50 to 500 times, from 30 to 400 times, from 35 to 300 times, from 1 to 75 times, from 1.5 to 50 times, from 2 to 30 times, or from 2 to 15 times the electromagnetic radiation penetration depth into the fluid in the flow path. The average linear distance between the outer surface of the quartz tube 215 and the inner surface of the reactor wall 220 can be configured to be a factor of the electromagnetic radiation penetration depth into the fluid in the flow path 210 for any electromagnetic radiation, electromagnetic radiation wavelength, or average electromagnetic wavelength disclosed herein. For example, in some embodiments, the average linear distance between the outer surface of the quartz tube 215 and the inner surface of the reactor wall 220 can be configured for any penetration depth disclosed herein when applied to 253 to 256 nm, 265 to 266 nm, or 296 to 298 nm electromagnetic radiation wavelengths.

The electromagnetic radiation penetration depth into the fluid in the flow path can be determined using the Beer-Lambert law, $A=\varepsilon l\, c$, where A is the absorbance, $\varepsilon$ is the molar absorption or extinction coefficient (L/mol-cm), l is the path length (cm), and c is the concentration of the absorbing species (mol/L). The penetration depth can be impacted by, for example, the tube composition, the tube wall thickness, the composition of the fluid in the flow path, the electromagnetic wavelength, and/or the electromagnetic radiation source power. When using an ultraviolet light source, the ultraviolet light radiation penetration depth can be determined, for example, as an average over the wavelength range of 253-256 nm; alternatively, over the wavelength range of 265-266 nm; or alternatively, over the wavelength range of 296-298 nm. Other appropriate wavelengths (or ranges of wavelengths) for the respective electromagnetic radiation source(s) can be readily determined by those of skill in the art in view of the factors disclosed herein.

For certain fluid compositions contemplated herein, the electromagnetic radiation penetration depth into the fluid can be relatively small. Hence, in some embodiments, the average linear distance between the outer surface of the tube 215 and the inner surface of the reactor wall 220 can be less than or equal to 15 cm, 12.5 cm, 10 cm, 7.5 cm, 5 cm, 4.5 cm, 4 cm, 3.5 cm, 3 cm, 2.5 cm, 2 cm, 1.5 cm, or 1 cm, or greater than or equal to 0.35 cm, 0.4 cm, 0.5 cm, 0.6 cm, 0.7 cm, 0.8 cm, 1 cm, 1.5 cm, 2 cm, 2.5 cm, 3 cm, 4 cm, 5 cm, or 6 cm. The average linear distance between the outer surface of the tube 215 and the inner surface of the reactor wall 220 can range from any minimum value disclosed herein to any maximum value disclosed herein. Accordingly, illustrative ranges for this average linear distance can include, but are not limited to, from 0.35 to 15 cm, from 0.4 to 10 cm, from 0.5 to 5 cm, from 0.6 cm to 8 cm, from 0.5 to 3 cm, from 0.5 cm to 1.5 cm, from 0.7 to 10 cm, from 0.7 to 5 cm, from 0.7 to 1.5 cm, from 4 to 9 cm, from 4 to 6 cm, or from 6 to 9 cm, and the like. Other average linear distances between the outer surface of the tube 215 and the inner surface of the reactor wall 220 are readily apparent from the present disclosure In another embodiment, the flow reactor vessel 200 can be configured to have a maximum ratio of the cross-sectional area of the inner surface of the reactor wall 220 to the cross-sectional area of the outer surface of the tube 215 of 25:1, 20:1, 15:1, 12:1, 10:1, 7:1, 5:1, 4:1, 3:1, or 2:1. In yet another embodiment, the minimum ratio of the cross-sectional area of the inner surface of the reactor wall 220 to the cross-sectional area of the outer surface of the tube 215 can be 1.2:1, 1.4:1, 1.6:1, 2:1, 3:1, 4:1, 6:1, or 8:1. The cross-section is in the transverse direction, such as is illustrated in FIG. 2B. The flow reactor vessel 200 can be configured to have a ratio of the cross-sectional areas ranging from any minimum ratio of the cross-sectional area of the inner surface of the reactor wall 220 to the outer surface of the tube 215 disclosed herein to any maximum ratio of the cross-sectional area of the inner surface of the reactor wall 220 to the outer surface of the tube 215 disclosed herein. For example, suitable ranges for this ratio of cross-sectional areas can include, but are not limited to, the following ranges: from 1.2:1 to 15:1, from 1.6:1 to 12:1, from 1.6:1 to 8:1, from 1.2:1 to 7:1, from 1.6:1 to 4:1, from 1.2:1 to 4:1, from 1.2:1 to 2:1, from 1.3:1 to 3:1, or from 1.4:1 to 4:1, and the like. Other ratios of the cross-sectional area of the inner surface of the reactor wall 220 to the cross-sectional area of the outer surface of the tube 215 are readily apparent from the present disclosure. When the ratio of the cross-sectional area of the inner surface of the reactor wall 220 to the cross-sectional area of the outer surface of the tube 215 is not uniform, the ratio of the cross-sectional area of the inner surface of the reactor wall 220 to the cross-sectional area of the outer surface of the tube 215 can be an average ratio of the cross-sectional area of the inner surface of the reactor wall 220 to the cross-sectional area of the outer surface of the tube 215.

In another embodiment, the flow reactor vessel 200 can be configured to have a relatively small flow area 210, one measure of which can be a cross-sectional area of the region (e.g., the annular region in FIG. 2B) between the outer surface of the tube 215 and the inner surface of the reactor wall 220 that is less than or equal to 750 cm$^2$, 600 cm$^2$, 500 cm$^2$, 400 cm$^2$, 300 cm$^2$, 250 cm$^2$, 200 cm$^2$, 150 cm$^2$, 100 cm$^2$, 80 cm$^2$, 60 cm$^2$, 50 cm$^2$, 40 cm$^2$, 30 cm$^2$, 25 cm$^2$, or 20 cm$^2$. In some embodiments, the minimum cross-sectional area can be 5 cm$^2$, 7.5 cm$^2$, 10 cm$^2$, 15 cm$^2$, 20 cm$^2$, 25 cm$^2$, 50 cm$^2$, 75 cm$^2$, 100 cm$^2$, 125 cm$^2$ $^2$, 150 cm, 200 cm$^2$, or 250 cm$^2$. As above, this cross-section is in the transverse direction. The cross-sectional area of the region (e.g., the annular region in FIG. 2B) between the outer surface of the tube 215 and the inner surface of the reactor wall 220 can range from any minimum cross-sectional area disclosed herein to any maximum cross-sectional area disclosed herein. Exemplary ranges for this cross-sectional area can include, but are not limited to, the following ranges: from 5 to 750 cm$^2$, from 7.5 to 600 cm$^2$, from 10 to 400 cm$^2$, from 15 to 80 cm$^2$, from 15 to 60 cm$^2$, from 125 to 400 cm$^2$, from 125 to 250 cm$^2$, from 10 to 100 cm$^2$, from 10 to 25 cm$^2$, or from 250 to 400 cm$^2$, and the like. Other cross-sectional area ranges are readily apparent from the present disclosure.

Figure 3:
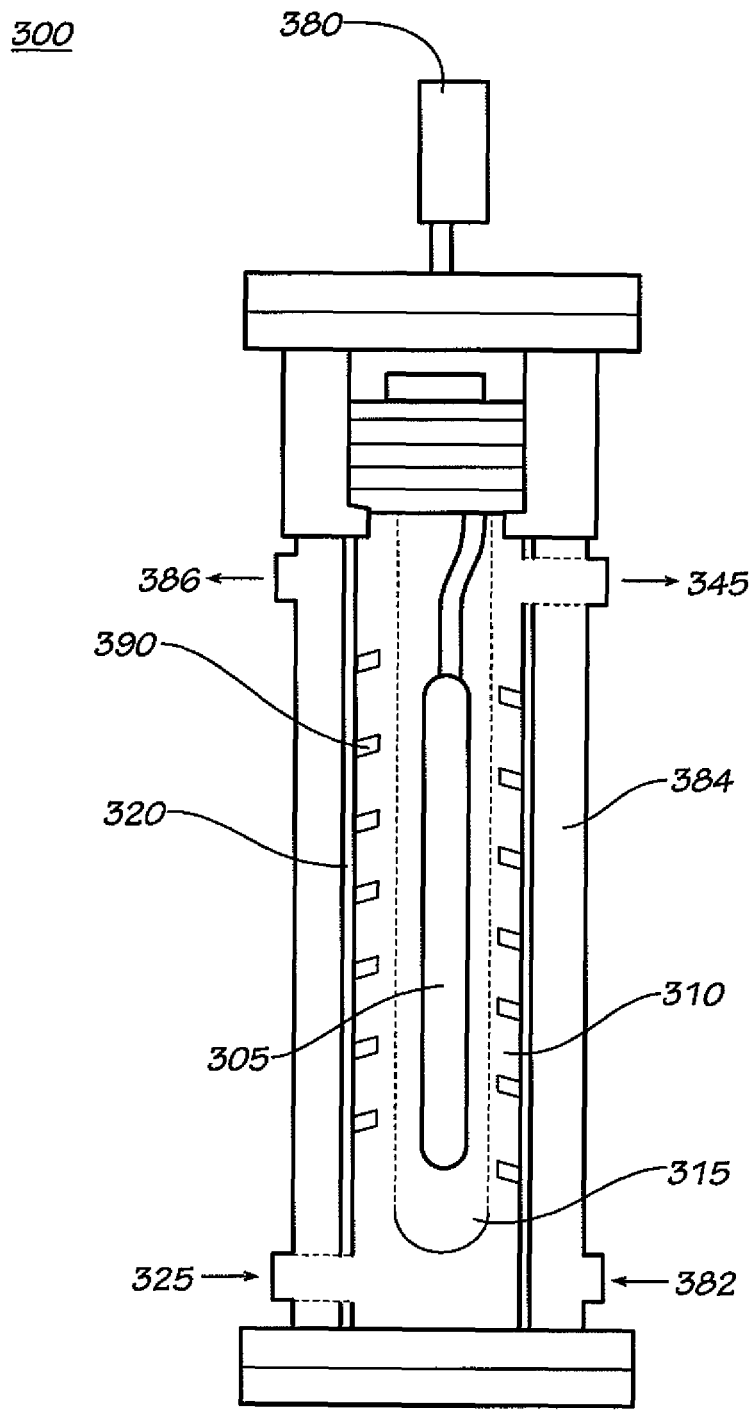
FIG. 3 shows a partial cross-sectional view of a flow reactor vessel in yet another embodiment of the present invention.

FIG. 3 illustrates yet another embodiment of a flow reactor vessel, shown with a vertical orientation. Similar to relation to FIG. 1, FIG. 2A, and FIG. 2B, the flow reactor vessel 300 of FIG. 3 can include an outer wall 320, a quartz tube 315, a UV lamp 305, a flow area 310 between the wall and the tube, an inlet 325, an outlet 345, and an electrical connection 380, generally the same as described above in relation to FIG. 1, FIG. 2A, and FIG. 2B.

In view of the comparative size of the flow path 310 and the electromagnetic radiation penetration depth, it can be beneficial in certain embodiments to have turbulent flow of the fluid in the flow path. Turbulent flow can increase the mixing and the amount of the fluid flowing through the flow reactor vessel that is exposed to radiation and/or contacts the outer surface of the quartz tube 315. Moreover, turbulent flow can improve heat removal from (cooling of) the quartz tube and can result in a longer lifetime of the UV lamp. In some embodiments, the flow reactor vessel can be configured to result in a fluid flow rate in the flow path of a Reynolds number of at least 4,000, at least 5,000, at least 10,000, at least 25,000, or at least 50,000. For instance, suitable ranges for the Reynolds number can include, but are not limited to, from 4,000 to 300,000, from 5,000 to 250,000, from 4,000 to 200,000, from 5,000 to 200,000, from 10,000 to 250,000, or from 25,000 to 200,000, and the like.

Although not required, flow-affecting elements, such as baffles or surface disruptions, can be present in the flow path to promote turbulent flow of the fluid. In FIG. 3, baffles 390 are included in the flow reactor vessel 300 to promote turbulent flow in the annular flow area 310 between the quartz tube 315 and the reactor wall 320. It should be noted that flow-affecting elements can be used when the flow rate in the flow path does not have a Reynolds number which promotes turbulent flow; or alternatively, flow-affecting elements can be used when the flow rate in the flow path would be sufficient to promote turbulent flow in the absence of the flow-affecting elements.

The reactor design of FIG. 3 illustrates the flow reactor vessel 300 with an integrated heat exchange system, for controlling temperature within the reaction chamber, with the heat exchange system generally surrounding the reactor wall 320 of the reaction chamber. The heat exchange system can surround any portion, or all, of the reaction chamber. A coolant or heat transfer fluid inlet 382 and exit 386 can be provided, as well as a coolant flow area 384, as shown in FIG. 3. In other embodiments, any portion, or all, of the flow reactor vessel can be immersed or surrounded by a heat exchange medium that is not an integral part of the flow reactor vessel. In other embodiments, the heat exchange system does not have to be integrated into the flow reactor vessel. For example, a flow reactor vessel (or multiple flow reactor vessels), without an integrated heat exchange system, can be placed inside another vessel or apparatus which can provide the heat exchange for the flow reactor vessel (or multiple flow reactor vessels).

It should be noted that FIG. 1, FIGS. 2A-2B, and FIG. 3 represent three possible designs for a flow reactor vessel. Minimally, the flow reactor vessel comprises (a) a reaction chamber comprising a reactor wall, an inlet for a fluid, and an outlet; (b) a tube positioned within the reaction chamber, a flow path for the fluid including a region between an outer surface of the tube and an inner surface of the reactor wall; and (c) an electromagnetic radiation source enclosed within the tube, the electromagnetic radiation source configured to deliver radiation into the fluid in the flow path. Contemplated flow reactor vessels can utilize any other flow reactor vessel features described herein and/or shown in FIG. 1, FIGS. 2A-2B, and FIG. 3, in any combination. For example, in an embodiment, the flow reactor vessel of FIG. 1 and/or FIG. 2A can further comprise baffles or mixing elements and/or an integrated heat exchange system; or alternatively, the flow reactor vessel of FIG. 3 can include a retainer assembly to minimize or prevent wobble and/or deflection of the tube positioned within the reaction chamber, and/or exclude baffles, and/or exclude an integrated heat exchange system. All combinations of the various aspects, and/or embodiments, and/or features disclosed herein can be combined to describe inventive flow reactor vessels of the present application.

Also encompassed herein are flow reactor systems, and such systems generally can comprise two or more of any of the flow reactor vessels described hereinabove, whether configured in series, in parallel, or any combination thereof. For example, an exemplary flow reactor system can comprise two or more flow reactor vessels in series. In one embodiment, the flow reactor system can comprise a single pass through each flow reactor vessel, while in another embodiment, the flow reactor system can comprise more than one pass through each flow reactor vessel. For temperature control of the flow reactor system, the flow reactor system can comprise a heat exchanger before and/or after each flow reactor vessel. Alternatively, two or more flow reactor vessels can be surrounded, either in whole or in part, by a single heat exchanger.

Processes for Producing Thiol Compounds

Embodiments of this invention are directed to processes for forming a thiol compound. Such processes can comprise, consist essentially of, or consist of (i) introducing a fluid comprising $H_2S$ and a compound having a carbon-carbon double bond (i.e., at least one) into the inlet and the flow path of any of the flow reactor vessels described herein; (ii) exposing the fluid to electromagnetic radiation within the reaction chamber to form a thiol compound; and (iii) discharging a composition comprising the thiol compound from the reaction chamber via the outlet. Generally, the features of the process (e.g., the compound having one or more carbon-carbon double bonds, the hydrogen sulfide to carbon-carbon double bond ratio, the components of and/or features of the fluid, and the conditions under which the thiol compound is formed, among others) are independently described herein and these features can be combined in any combination to further describe the disclosed process.

In some embodiments, the fluid of step (i) can contain a contact product of the compound having the carbon-carbon double bond and $H_2S$, as well as additional unrecited materials (e.g., a phosphite compound, an organic reaction medium, etc.). In any embodiment in which the fluid can make more that one pass through the flow reactor vessel and/or the fluid can pass through more than one flow reactor vessel arranged in series, the fluid of step (i) can further comprise a thiol compound. Moreover, it is contemplated that the processes for forming thiol compounds can employ a fluid containing more than one compound having a carbon-carbon double bond.

In the processes disclosed herein, the molar ratio of $H_2S$ to carbon-carbon double bonds of the compound having a carbon-carbon double bond can be in a range from 5:1 to 500:1, or from 15:1 to 500:1, or from 20:1 to 500:1. In some embodiments, the molar ratio of $H_2S$ to carbon-carbon double bonds of the compound having a carbon-carbon double bond can be in a range from 15:1 to 200:1, while in other embodiments, the molar ratio can be in a range from 15:1 to 150:1. Molar ratios of $H_2S$ to carbon-carbon double bonds of the compound having a carbon-carbon double bond falling within the range from 20:1 to 200:1, or from 20:1 to 100:1, or from 20:1 to 75:1, or from 20:1 to 50:1, or from 25:1 to 50:1, also can be employed in embodiments of this invention. In embodiments where the fluid makes multiple passes through the flow reactor vessel, or passes through multiple flow reactor vessels arranged in series, these molar ratios will increase as the reaction proceeds (and more thiol compound is produced). Accordingly, these molar ratio ranges can be for the initial fluid charge, prior to any exposure of the fluid to electromagnetic radiation within the reaction chamber, and any subsequent formation of a thiol compound; or alternatively, the molar ratio ranges can be for the molar ratio at any point in the formation of the thiol compound.

When present in the fluid, the phosphite compound can be used at a molar ratio of the phosphite compound to carbon-carbon double bonds of the compound having a carbon-carbon double bond in a range from 0.00025:1 to 1:1, from 0.0005:1 to 0.50:1, from 0.0005:1 to 0.10:1, or from 0.001:1 to 0.10:1. In some embodiments, the molar ratio of the phosphite compound to carbon-carbon double bonds of the compound having a carbon-carbon double bond can be in a range from 0.006:1 to 0.05:1; alternatively, from 0.01:1 to 0.05:1; alternatively, from 0.01:1 to 0.04:1; or alternatively, from 0.01:1 to 0.03:1. As with the molar ratio of $H_2S$, these phosphite molar ratio ranges can be for the initial fluid charge, prior to any exposure of the fluid to electromagnetic radiation within the reaction chamber, and any subsequent formation of a thiol compound; or alternatively, the molar ratio ranges can be for the molar ratio at any point in the formation of the thiol compound.

In an embodiment, step (ii) of the process for forming a thiol compound can be conducted at a temperature of at least 0° C., at least 10° C., at least 15° C., at least 20° C., at least 25° C., or at least 30° C. For instance, the fluid can be irradiated within the reaction chamber with electromagnetic radiation at a temperature in a range from 0° C. to 150° C.; alternatively, from 10° C. to 125° C.; alternatively, from 15° C. to 100° C.; alternatively, from 25° C. to 100° C.; alternatively, from 30° C. to 100° C.; or alternatively, from 20° C. to 80° C.

In an embodiment, the pressure in the reaction chamber can be any pressure sufficient to maintain $H_2S$ in the liquid phase during the exposing step. However, in another embodiment, the exposing step can be conducted at a reaction pressure such as from 1.72 to 13.79 MPa, from 2.07 to 13.79 MPa, from 1.72 to 10.34 MPa, from 2.07 to 10.34 MPa, from 1.72 to 6.89 MPa, or from 2.07 to 5.17 MPa. In yet another embodiment, the exposing step can be conducted at reaction pressure, for instance, from 0.1 to 3.44 MPa, 0.14 to 1.38 MPa, from 0.14 to 1.03 MPa, from 0.14 to 0.69 MPa, from 0.14 to 0.52 MPa, or from 0.17 to 1.03 MPa. Further, the exposing step can be conducted at or above any minimum pressure disclosed herein, at or below any maximum pressure disclosed, or in any pressure range disclosed herein, for which the flow reactor vessel can be configured.

In some embodiments, the flow of the fluid in the flow path within the flow reactor vessel can be turbulent, and this flow property can further characterized by the Reynolds number. Accordingly, the flow rate of the fluid can be at a Reynolds number of at least 4,000, at least 5,000, at least 10,000, at least 25,000, or at least 50,000. Suitable ranges for the Reynolds number can include, but are not limited to, from 4,000 to 300,000, from 5,000 to 250,000, from 4,000 to 200,000, from 5,000 to 200,000, from 10,000 to 250,000, or from 25,000 to 200,000. In other embodiments, the flow reactor vessel can include baffles in the flow path to promote turbulent flow. In embodiments wherein the flow reactor vessel includes baffles in the flow path, the Reynolds number can be less than a Reynolds number necessary to provide turbulent flow; for example, a Reynolds number less than 10,000, less than 5,000, less than 4,000, less than 3,000, less than 2,000, or less than 1,000. Further, the flow rate of the fluid can at or above any minimum Reynolds number disclosed herein, at or below any maximum Reynolds number disclosed herein, or in any Reynolds number range disclosed herein.

In embodiments of this invention, the thiol compound can be formed in the presence of electromagnetic radiation. For instance, the thiol compound can be formed in the presence of ultraviolet light. Additionally or alternatively, the thiol compound can be formed by light photolysis initiation of a free radical initiator. Additionally or alternatively, the thiol compound can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The thiol compound can be formed in the presence of free radicals from any one of aforementioned sources, including combinations thereof, but is not limited to free radicals generated only by these means.

When the electromagnetic radiation is ultraviolet light, ultraviolet light in the range, for example, from 172 to 450 nm, from 185 to 380 nm, from 200 to 350 nm, or from 245 to 300 nm, can be employed. Ultraviolet light can be supplied from ultraviolet lamps, but other sources of ultraviolet light can be employed, and are to be considered within the scope of the present invention.

The free radical initiator can be any free radical initiator capable of forming free radicals under thermal decomposition or light (e.g., UV, visible, and/or IR, among others) photolysis. For example, the free radical initiator employed for the formation of the thiol compound can comprise a —N=N— group, a —O-O— group, or combinations thereof; alternatively, a —N=N— group; or alternatively, a —O-O— group. Free radical initiators, therefore, can include, but are not limited to, peroxy compounds, organic azo compounds, and the like, or combinations thereof; alternatively, peroxy compounds; or alternatively, organic azo compounds. Peroxy compounds which can be utilized can include peroxides, hydroperoxides, peroxyesters, diacylperoxides, and percarbonates; alternatively, peroxides; alternatively, hydroperoxides; alternatively, peroxyesters; alternatively, diacylperoxides; or alternatively, percarbonates. In an embodiment, the peroxide can be a dialkyl peroxide. In an embodiment, the hydroperoxide can be an alkyl hydroperoxide. In an embodiment, the peroxy ester can be an alkyl peroxyalkanoate, or alternatively, an alkyl peroxyarenoate. In an embodiment, the diacylperoxide can be a diaroyl peroxide, or alternatively, a diakoyl peroxide. In an embodiment, the percarbonate can be a dihydrocarbyl percarbonate; alternatively, a diarylpercarbonate; or alternatively, a dialkylpercarbonate. Generally, the hydrocarbon and/or alkane group(s) utilized in any peroxy compound can be a $C_1$ to $C_{30}$, $C_2$ to $C_{18}$, $C_2$ to $C_{10}$, or $C_2$ to $C_5$ hydrocarbon and/or alkane group(s). Generally, the arene group utilized in any peroxy compound can be a $C_6$ to $C_{30}$, $C_6$ to $C_{18}$, $C_6$ to $C_{15}$, or $C_6$ to $C_{10}$ arene group(s). Illustrative non-limiting examples of peroxy compounds which can be utilized can include, but are not limited to, diisobutyryl peroxide, 1-(2-ethylhexanoylperoxy)-1,3-dimethylbutyl peroxypivalate, cumylperoxyneodecanoate, 1,1,3,3-tetramethylbutyl peroxyneodecanoate, t-butyl peroxyneodecanoate, 1,1,3,3-tetramethylbutyl peroxypivalate, t-butyl peroxyneoheptanoate, t-amyl peroxypivalate, t-butyl peroxypivalate, di(3,5,5-trimethylhexanoyl) peroxide, dilauroyl peroxide, didecanoyl peroxide, 2,5-dimethyl-2,5-di(2-ethylhexanoylperoxy)hexane, 1,1,3,3-tetramethylbutyl peroxy 2-ethylhexanoate, t-amyl peroxy 2-ethylhexanoate, dibenzoyl peroxide, acetyl peroxide t-butyl peroxy 2-ethylhexanoate, t-butyl peroctanoate, t-butyl peroxydiethylacetate, t-butyl peroxyisobutyrate, t-butyl peroxy 3,5,5-trimethylhexanoate, t-butyl peroxyacetate, t-butyl peoxybenzoate, 2,4-dichlorobenzoyl peroxide, t-butylpermaleic acid, di-t-butyl diperphthalate, di(4-t-butylcyclohexyl) peroxydicarbonate, di(2-ethylhexyl) peroxydicarbonate, dibutyl peroxy-dicarbonate, dicetyl peroxydicarbonate, dimyristyl peroxydicarbonate, t-amylperoxy 2-ethylhexyl carbonate, t-butylperoxy isopropyl carbonate, t-butylperoxy 2-ethylhexyl carbonate, 1,1-di(t-butylperoxy) 3,5,5-trimethylcyclohexane, 2,2-di(4,4-di(t-butylperoxy)-cyclohexyl)propane, 1,1-di(t-butylperoxy) cyclohexane, 2,2-di(t-butylperoxy)butane, di(t-amyl) peroxide, dicumyl peroxide, di(t-butylperoxyisopropyl) benzene, 2,5-dimethyl-2,5-di(t-butylperoxy)hexane, t-butyl cumyl peroxide, 2,5-dimethyl-2,5-di(t-butylperoxy)hexyne-3,di-t-butyl peroxide, 3,6,9-triethyl-3,6,9-trimethyl-1,4,7-triperoxoane, t-butyl hydroperoxide, methyl benzyl hydroperoxide, octylperbenzoate, methyl ethyl ketone peroxide, acetone peroxide, and the like, or combinations thereof.

Non-limiting examples of suitable azo compounds include α,α'-azo diisobutyronitrile (AIBN), azobenzene, azomethane, 2,2'-azodi(2-methylbutyronitrile), 2,2'-azobis(4-methoxy-2,4-dimethyl valeronitrile), dimethyl 2,2'-azobis(-methylpropionate), 1,1'-azobis-(cyclohexane-1-carbonitrile), 1-[(cyano-1-methylethyDazol formamide, 2,2'- azobis(N-cyclohexyl-2-methylpropionamide), 2,2'-azobis (2,4-dimethyl valeronitrile), 2,2'-azobis(2-methylbutyronitrile), 2,2'-azobis [N-(2-propenyl-2-methylpropionamide], 2,2'-azobi s (N-butyl-2-methylproionamide), 2,2'-azobis{2-methyl-N-[1,1-bis (hydroxymethyl-2-hydroxy-ethyl] propionamide, 2,2'-azobis [2-methyl-N-(2-hydroxy ethy)propionamide], 2,2'-azobis [2-(2-imidazolin-2-yl)propane], 2,2'-azobis{2-methyl-N-[2-(1-hydroxybutyl)] propionamide}, 2,2'-azobis(-methylpropionitrile), 4,4'-azobis(-cyanovaleric acid), 2,2'-azobis(2-methylpropane), 2,2'-azobis(2-methylpropionamidine)dihydrochloride, methylpropionitrile, azodicarboxamide, and the like, or combinations thereof.

Generally, the peroxide and azo compound free radical initiators that can be utilized in accordance with the present invention decompose under first order kinetics. Skilled artisans can readily find the first order kinetic parameters which can be utilized to describe the decomposition of a particular free radical catalyst from sources such as chemical suppliers, industry reference publications, and/or open literature publications. Under first order kinetics, the time required for a given fraction (or percentage) of the free radical initiator to decompose, at a specific temperature, into initiating species is independent of the concentration of the free radical. This phenomenon is often stated as a half-life; that is, the time in which one-half of the free radical initiator decomposes under specific conditions (e.g., temperature). According to the first order kinetics, the half-life of a free radical initiator is defined as the time it takes one-half of the initiator to decompose at a particular temperature. Using the available first order kinetic parameters for a particular free radical initiator, the concentration of the free radical initiator present in the reaction mixture can be determined at a particular time during the reaction based upon the knowledge of the amount of free radical initiator added to the reaction, the times at which additional (if any) free radical initiator is added to the reaction, and the temperature profile of the reaction.

When the thiol compound is formed under conditions utilizing the thermal decomposition of a free radical initiator, the thiol compound can be formed at a temperature within a temperature range of the 1 hour half-life of the free radical initiator. Alternatively, when the thiol compound is formed under conditions utilizing the thermal decomposition of a free radical initiator, the thiol compound can be formed using a free radical initiator having a half-life within a time range at the temperature utilized to form the thiol compound. For example, the process can be conducted at a temperature within ±25° C. of the 1 hour half-life of the free radical initiator. In other embodiments, the thiol compound can be formed at a temperature within ±20° C. of the 1 hour half-life of the free radical initiator; alternatively, at a temperature within ±15° C. of the 1 hour half-life of the free radical initiator; alternatively, at a temperature within ±10° C. of the 1 hour half-life of the free radical initiator. In another embodiment, the thiol compound can be formed using a free radical initiator having a half-life within a range from 0.1 to 10 hours at the temperature the thiol compound is formed. Alternatively, the thiol compound can be formed using a free radical initiator having a half-life ranging from 0.1 to 10 hours, from 0.25 to 4 hours, or from 0.5 to 2 hours, at the temperature the thiol compound is formed. Generally, the thiol compound can be formed at or above any minimum temperature disclosed herein or in any temperature range disclosed herein. In some embodiments of this invention, the thiol compound can be formed at a temperature in a range from 0° C. to 150° C.; alternatively, from 10° C. to 125° C.; alternatively, from 15° C. to 100° C.; alternatively, from 25° C. to 100° C.; alternatively, from 30° C. to 100 ° C.; or alternatively, from 20° C. to 80° C.

Depending upon the particular free radical initiator, a free radical initiator can produce a different number of free radical reaction-initiating species per mole of free radical initiator; thus, the concentration of the free radical initiator can be stated in terms which describe the number of free radical reaction-initiating species generated per mole of free radical initiator. The term "equivalent" is often used to describe the number of reaction-initiating species produced per mole of free radical initiator. For example, one skilled in the art will readily recognize that di-t-butylperoxide can generate two free radical reaction-initiating species per mole of di-t-butylperoxide, while 2,5-bis(t-butylperoxy)-2,5-dimethylhexane can generate four free radical reaction-initiating species per mole of 2,5-bis(t-butylperoxy)-2,5-dimethylhexane.

In some embodiments, a photoinitiator can be utilized. Commercially available photoinitiators include, by way of example, Irgacure® 184 (1-hydroxy-cyclohexyl-phenyl-ketone), Irgacure® 500 (50% 1-hydroxy-cyclohexyl-phenyl-ketone and 50% benzophenone), Irgacure® 819 (Bis-(2,4,6-trimethylbenzoyl)-phenylphosphineoxide), and Irgacure® 127 (2-hydroxy-1- 14-14-(2-hydroxy-2-methyl-propionyl)-benzyl]-phenyl }-2-methyl-propan-1-one), all available from Ciba Specialty Chemicals, and Duracure 1173 (2-hydroxy-2-methyl-1-phenyl-1-propanone).

When a free radical initiator is present in the fluid, the weight percentage of the free radical initiator, based on the weight of the compound having a carbon-carbon double bond, can be in a range from 0.05 to 10 wt. %, from 0.1 to 9 wt. %, from 0.2 to 5 wt. %, or from 0.1 to 2 wt. %. When a photoinitiator is present in the fluid, the weight percentage of the photoinitiator, based on the weight of the compound having a carbon-carbon double bond, can be in a range from 0.01 to 5 wt. %, from 0.05 to 5 wt. %, from 0.5 to 3 wt. %, or from 1 to 4 wt. %. Other amounts of the free radical initiator and/or the photoinitiator can be employed depending on the specific conditions used in the process (e.g., temperature, pressure, Reynolds number) and the respective amounts of $H_2S$ and phosphite compound that may be used, amongst other factors. These weight percentage ranges can be for the initial fluid charge, prior to any exposure of the fluid to electromagnetic radiation within the reaction chamber, and any subsequent formation of a thiol compound; or alternatively, these weight percentage ranges can be for the weight percentage at any point in the formation of the thiol compound. It is contemplated that more than one free radical initiator, more than one photoinitiator, or combinations of free radical initiator(s) and photoinitiator(s), can be employed.

In an embodiment, the fluid can be substantially free of an organic reaction medium. However, in other embodiments, the fluid can comprise an organic reaction medium. Generally, the organic reaction medium can be a material which does not react, to a significant extent, under the utilized reaction conditions. Typically, when used, the organic reaction medium can be present in an amount up to 1,000 wt. %, based on the weight of the compound having at least one carbon-carbon double bond. Alternatively, the organic reaction medium can be present in an amount up 750 wt. %, up to 500 wt. %, up to 250 wt. %, up to 200 wt. %, up to 150 wt. %, or up to 100 wt. % based on the weight of the compound having at least one carbon-carbon double bond. When an organic reaction medium is utilized, the minimum amount utilized can be at least 5 wt. %, at least 10 wt. %, at least 25 wt. %, at least 50 wt. %, or at least 75 wt. %, based on the weight of the compound having at least one carbon-carbon double bond. Generally, the amount of the organic reaction medium that can be utilized can be in a range from any minimum amount of organic reaction medium described herein to any maximum amount of organic reaction medium described herein. In some non-limiting embodiments, the range of the organic reaction medium which can be utilized can be from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the compound having a carbon-carbon double bond. These weight percentage ranges can be for the initial fluid charge, prior to any exposure of the fluid to electromagnetic radiation within the reaction chamber, and any subsequent formation of a thiol compound; or alternatively, the weight percentage ranges can be for the weight percentage at any point in the formation of the thiol compound.

Processes for Producing Sulfide Compounds

Embodiments of this invention also are directed to processes for forming a sulfide compound (a compound with at least one —S— group). Such processes can comprise, consist essentially of, or consist of (i) introducing a fluid comprising a mercaptan compound and a compound having a carbon-carbon double bond (i.e., at least one) into the inlet and the flow path of any of the flow reactor vessels described herein; (ii) exposing the fluid to electromagnetic radiation within the reaction chamber to form a sulfide compound; and (iii) discharging a composition comprising the sulfide compound from the reaction chamber via the outlet. Generally, the features of the process (e.g., the mercaptan compound, the compound having one or more carbon-carbon double bonds, the SH to carbon-carbon double bond ratio, the components of and/or features of the fluid, and the conditions under which the sulfide compound is formed, among others) are independently described herein and these features can be combined in any combination to further describe the disclosed process.

In some embodiments, the fluid of step (i) can contain a contact product of the compound having the carbon-carbon double bond and the mercaptan compound, as well as additional unrecited materials (e.g., a phosphite compound, an organic reaction medium, etc.). In any embodiment in which the fluid can make more that one pass through the flow reactor vessel and/or the fluid can pass through more than one flow reactor vessel arranged in series, the fluid of step (i) can further comprise a sulfide compound. Moreover, it is contemplated that the processes for forming sulfide compounds can employ a fluid containing more than one compound having a carbon-carbon double bond and/or more than mercaptan compound.

In the processes disclosed herein, the molar ratio of SH of the mercaptan compound to carbon-carbon double bonds of the compound having a carbon-carbon double bond is not limited to any particular range. In some embodiments, however, the molar ratio can be in a range from 10:1 to 1:10, or from 5:1 to 1:5, or from 4:1 to 1:4. Other suitable ranges for the molar ratio of SH of the mercaptan compound to carbon-carbon double bonds of the compound having a carbon-carbon double bond can include, but are not limited to, from 3:1 to 1:3, or from 2:1 to 1:2, or from 1.5:1 to 1:1.5, or from 1.3:1 to 1:1.3, or from 1.2:1 to 1:1.2, or from 1.1:1 to 1:1.1. For example, the molar ratio of SH of the mercaptan compound to carbon-carbon double bonds of compound having a carbon-carbon double bond can be in a range from 1:1.05 to 1:1.2, such that there is a molar excess of the compound having a carbon-carbon double bond. In embodiments where the fluid makes multiple passes through the flow reactor vessel, or passes through multiple flow reactor vessels arranged in series, these molar ratios can change as the reaction proceeds (and more sulfide compound is produced). Accordingly, these molar ratio ranges can be for the initial fluid charge, prior to any exposure of the fluid to electromagnetic radiation within the reaction chamber, and any subsequent formation of a sulfide compound; or alternatively, the molar ratio ranges can be for the molar ratio at any point in the formation of the sulfide compound.

When present in the fluid, other materials such as a phosphite compound, a free radical initiator, a photoinitiator, and/or an organic reaction medium, can be used as disclosed herein in relation to the processes for the formation of thiol compounds, and can be present at any amounts in the respective ranges disclosed herein.

In an embodiment, step (ii) of the process for forming a sulfide compound can be conducted at a temperature of at least 0° C., at least 10° C., at least 15° C., at least 20° C., at least 25° C., or at least 30° C. For instance, the fluid can be irradiated within the reaction chamber with electromagnetic radiation in a range from 0° C. to 150° C.; alternatively, from 10° C. to 125° C.; alternatively, from 15° C. to 100° C.; alternatively, from 15° C. to 90° C.; alternatively, from 30° C. to 100° C.; alternatively, from 40° C. to 100° C.; alternatively, from 20° C. to 80° C.; or alternatively, from 25° C. to 60° C.

In an embodiment, the pressure in the reaction chamber can be any pressure sufficient to maintain the compound having the carbon-carbon double bond and the mercaptan compound in the liquid phase during the exposing step. In another embodiment, the exposing step can be conducted at a reaction pressure such as from 1.72 to 13.79 MPa, from 2.07 to 13.79 MPa, from 1.72 to 10.34 MPa, from 2.07 to 10.34 MPa, from 1.72 to 6.89 MPa, or from 2.07 to 5.17 MPa. In yet another embodiment, however, the exposing step can be conducted at a reaction pressure, for instance, from 0.1 to 3.44 MPa, 0.14 to 1.38 MPa, from 0.14 to 1.03 MPa, from 0.14 to 0.69 MPa, from 0.14 to 0.52 MPa, or from 0.17 to 1.03 MPa. Further, the exposing step can be conducted at or above any minimum pressure disclosed herein, at or below any maximum pressure disclosed, or in any pressure range disclosed herein, for which the flow reactor can be configured.

In some embodiments, the flow of the fluid in the flow path within the flow reactor vessel can be turbulent, and this flow property can be further characterized by the Reynolds number. Accordingly, the flow rate of the fluid can be at a Reynolds number of at least 4,000, at least 5,000, at least 10,000, at least 25,000, or at least 50,000. Suitable ranges for the Reynolds number can include, but are not limited to, from 4,000 to 300,000, from 5,000 to 250,000, from 4,000 to 200,000, from 5,000 to 200,000, from 10,000 to 250,000, or from 25,000 to 200,000. In other embodiments, the flow reactor vessel can include baffles in the flow path to promote turbulent flow. In embodiments wherein the flow reactor vessel includes baffles in the flow path, the Reynolds number can be less than a Reynolds number necessary to provide turbulent flow; for example, a Reynolds number less than 10,000, less than 5,000, less than 4,000, less than 3,000, less than 2,000, or less than 1,000. Further, the flow rate of the fluid can be at or above any minimum Reynolds number disclosed herein, at or below any maximum Reynolds number disclosed herein, or in any Reynolds number range disclosed herein.

In embodiments of this invention, the sulfide compound can be formed in the presence of electromagnetic radiation. For instance, the sulfide compound can be formed in the presence of ultraviolet light. Additionally or alternatively, the sulfide compound can be formed by light photolysis initiation of a free radical initiator. Additionally or alternatively, the sulfide compound can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The sulfide compound can be formed in the presence of free radicals from any one of aforementioned sources, including combinations thereof, but is not limited to free radicals generated only by these means. When the electromagnetic radiation is ultraviolet light, ultraviolet light in the range, for example, from 172 to 450 nm, from 185 to 380 nm, from 200 to 350 nm, or from 245 to 300 nm, can be employed. Ultraviolet light can be supplied from ultraviolet lamps, but other sources of ultraviolet light can be employed, and are to be considered within the scope of the present invention.

Further embodiments of this invention also are directed to processes for forming a sulfide compound (a compound with at least one —S— group). Such processes can comprise, consist essentially of, or consist of (i) introducing a fluid comprising a $H_2S$ and a compound having a carbon-carbon double bond (i.e., at least one) into the inlet and the flow path of any of the flow reactor vessels described herein; (ii) exposing the fluid to electromagnetic radiation within the reaction chamber to form a sulfide compound; and (iii) discharging a composition comprising the sulfide compound from the reaction chamber via the outlet. In some embodiments, the fluid of step (i) can contain a contact product of the compound having the carbon-carbon double bond and $H_2S$, the sulfide compound, as well as additional unrecited materials (e.g., a phosphite compound, an organic reaction medium, etc.). In any embodiment in which the fluid can make more than one pass through the flow reactor vessel and/or the fluid can pass through more than one flow reactor vessel arranged in series, the fluid of step (i) can further comprise a thiol compound and/or the sulfide compound.

Generally, the features of the process to form a sulfide compound from $H_2S$ and a compound having a carbon-carbon double bond can have the same features as the process to form a mercaptan from $H_2S$ and a compound having a carbon-carbon double bond as described herein, with the exception of the molar ratio of $H_2S$ to carbon-carbon double bonds of the compound having a carbon-carbon double bond. In an embodiment, the molar ratio of $H_2S$ to carbon-carbon double bonds of the compound having a carbon-carbon double bond can be in a range from 10:1 to 1:10, or from 5:1 to 1:5, or from 4:1 to 1:4, or from 3:1 to 1:3. In some embodiments, the molar ratio of $H_2S$ to carbon-carbon double bonds of the compound having a carbon-carbon double bond can be in a range from 0.75:2 to 1.25:2, or from 0.85:2 to 1.15:2, or from 0.9:2 to 1.1:2, or from 0.95:2 to 1.05:2. In another embodiment, the molar ratio of $H_2S$ to carbon-carbon double bonds of the compound having a carbon-carbon double bond can be about 1:2. Exemplary sulfide compounds that can be produced from $H_2S$ and a compound having a carbon-carbon double bond can include, for instance, symmetrical sulfides, such as diethyl sulfide, dipropryl sulfide, dibutyl sulfide, dipentyl sulfide, dihexyl sulfide, diheptyl sulfide, dioctyl sulfide, dinonyl sulfide, didecyl sulfide, didodecyl sulfide, and the like.

Compounds with Carbon-Carbon Double Bonds

The compound having at least one carbon-carbon double bond can be any compound which can be converted to a thiol compound and/or a sulfide compound utilizing a process and/or flow reactor vessel described herein. Generally, the compound having at least one carbon-carbon double bond can have any combination of the features for the compound having at least one carbon-carbon double bond described herein.

In an embodiment, the compound used in the process can have at least 2 carbon atoms, at least 3 carbon atoms, at 4 carbon atoms, or at least 5 carbon atoms. In some embodiments, the compound used in the process can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the compound used in the process can have from any minimum number of carbon atoms described herein to any maximum number of carbon atoms described herein. For example, in some non-limiting embodiments, the compound having at least one carbon-carbon double bond can have from 2 to 100 carbon atoms, from 3 to 80 carbon atoms, from 4 to 60 carbon atoms, or from 5 to 60 carbon atoms. Other carbon atom number ranges can be readily envisioned from the present disclosure and are encompassed herein.

In an embodiment, the compound having at least one carbon-carbon double bond can be a hydrocarbon compound, a heteroatomic compound, or any combination thereof; alternatively, a hydrocarbon compound; or alternatively, a heteroatomic compound. In some embodiments, the compound having at least one carbon-carbon double bond can be aliphatic, aromatic, or any combination thereof; alternatively, aliphatic; or alternatively, aromatic. In other embodiments, the compound having at least one carbon-carbon double bond can be acyclic, cyclic, or any combination thereof; alternatively, acyclic; or alternatively, cyclic.

The compound used in these processes has at least one carbon-carbon double bond. In one embodiment, the compound has from 1 to 10 double bonds; alternatively, from 1 to 8 double bonds; alternatively, from 2 to 6 double bonds; or alternatively, from 2 to 4 double bonds. In another embodiment, the compound has only one carbon-carbon double bond; alternatively, only two double bonds; alternatively, only three double bonds; alternatively, only four double bonds; alternatively, only five double bonds; or alternatively, only six double bonds.

Representative and non-limiting examples of compounds having only one carbon-carbon double bond can comprise, consist essentially of, or consist of, either singly or in any combination, ethylene, propylene, 1-butene, 2-butene, 3-methyl-1-butene, isobutylene, 1-pentene, 2-pentene, 3-methyl-l-pentene, 4-methyl-l-pentene, 1-hexene, 2-hexene, 3-ethyl-1- hexene, 1-heptene, 2-heptene, 3-heptene, 1-octene, 1-decene, 1-dodecene, or styrene.

Representative and non-limiting examples of cyclic compounds having only one carbon-carbon double bond can comprise, consist essentially of, or consist of, either singly or in any combination, cyclopentene, cyclohexene, cycloheptene, or cyclooctene. In some embodiments, cyclic compounds having only one carbon-carbon double bond can comprise, consist essentially of, or consist of, cyclopentene; alternatively, cyclohexene; alternatively, cycloheptene; or alternatively, cyclooctene.

Suitable examples of compounds having at least two carbon-carbon double bonds that may be employed in the processes disclosed herein can comprise, consist essentially of, or consist of, either singly or in any combination, butadiene, isoprene, cyclobutadiene, cyclopentadiene, cyclohexadiene, cyclooctadiene, norbornadiene, vinylcyclohexene, vinylnorbornene, divinylbenzene, or cyclopentadiene dimer. Hence, mixtures or combinations of more than one compound having at least two double bonds can be employed. Accordingly, the compound having at least two double bonds can comprise, consist essentially of, or consist of, either singly or in any combination, butadiene, isoprene, cyclobutadiene, cyclopentadiene, cyclohexadiene, or cyclooctadiene; alternatively, norbornadiene, vinylcyclohexene, vinylnorbornene, or divinylbenzene; alternatively, butadiene; alternatively, isoprene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an embodiment, the compound can comprise, consist essentially of, or consist of, one or more compounds having only three carbon-carbon double bonds. Illustrative non-limiting examples of such compounds can comprise, consist essentially of, or consist of, singly or in any combination, trivinylcyclohexane, trivinylbenzene, cycloheptatriene, dimethyl heptatriene, octatriene, cyclooctatriene, or cyclododecatriene. In one embodiment, the compound having only three double bonds can comprise, consist essentially of, or consist of, trivinylcyclohexane. In another embodiment, the compound having only three double bonds can comprise, consist essentially of, or consist of, trivinylbenzene. In another embodiment, the compound can comprise, consist essentially of, or consist of, cycloheptatriene. In another embodiment, the compound having only three double bonds can comprise, consist essentially of, or consist of, dimethyl heptatriene. In another embodiment, the compound having only three double bonds can comprise, consist essentially of, or consist of, octatriene. Yet, in another embodiment, the compound having only three double bonds can comprise, consist essentially of, or consist of, cyclooctatriene. In still another embodiment, the compound having only three double bonds can comprise, consist essentially of, or consist of, cyclododecatriene.

Compounds having four or more carbon-carbon bonds also are contemplated. For instance, the compound having four or more carbon-carbon bonds can comprise, consist essentially of, or consist of, cyclooctatetraene; alternatively, cyclododecatetraene; alternatively, a polybutadiene; or alternatively, a combination of two or more of these compounds.

Additionally, olefin metathesis products having two or more carbon-carbon double bonds can be utilized. As such, the compound having two or more double bonds can comprise, consist essentially of, or consist of, either singly or in any combination, an olefin metathesis product of one or more of vinylcyclohexene, vinylnorbornene, divinylbenzene, trivinylcyclohexane, trivinylbenzene, norbornene, norbornadiene, cyclooctadiene, trivinylcyclohexane, and cyclododecatriene. For instance, the compound having two or more carbon-carbon double bonds can comprise, consist essentially of, or consist of, an olefin metathesis product of vinylcyclohexene, an olefin metathesis product of vinylcyclohexene with vinylnorbornene, and so forth.

In an embodiment, the compound can comprise, consist essentially of, or consist of, a terpene compound having at least two carbon-carbon double bonds. For example, the compound having two or more double bonds can comprise, consist essentially of, or consist of, either singly or in any combination, a monoterpene, a sesquiterpene, a diterpene, a sesterpene, or a triterpene. Accordingly, the compound can comprise, consist essentially of, or consist of, a monoterpene or a sesquiterpene; alternatively, a monoterpene; alternatively, a sesquiterpene; alternatively, a diterpene; alternatively, a sesterpene; or alternatively, a triterpene. The hydrocarbon terpene can comprise, consist essentially of, or consist of, a cyclic terpene in some embodiments of this invention, while in other embodiments, the hydrocarbon terpene can comprise, consist essentially of, or consist of, an acyclic terpene.

The compound can comprise, consist essentially of, or consist of, either singly or in any combination, myrcene, ocimene (i.e., (E)-ocimene, (Z)-ocimene, or mixtures thereof), alloocimene, cosmene, limonene, terpinolene, terpinene (i.e., α-terpinene, γ-terpinene, or mixtures thereof), phellandrene (i.e., α-phellandrene, (β-phellandrene, or mixtures thereof), or 1,3,8-para-menthatriene; alternatively, myrcene; alternatively, ocimene; alternatively, alloocimene; alternatively, cosmene; alternatively, limonene (e.g., D-limonene); alternatively, terpinolene, alternatively, terpinene; alternatively, phellandrene; or alternatively, 1,3,8-para-menthatriene. Yet, in other embodiments, the compound can comprise, consist essentially of, or consist of, either singly or in any combination, farnesene (i.e., (E)-α-farnesene, (Z)-α-farnesene, (E)-β-farnesene, (Z)-β-farnesene, or mixtures thereof), bisabolene (i.e., α-bisabolene, β-bisabolene, or mixtures thereof), zingiberene, β-curcumene, laurene, elemene (i.e., α-elemene, γ-elemene, or mixtures thereof), humulene, germacrene, cadinene (i.e., α-cadinene, β-cadinene, γ-cadinene, or mixtures thereof), selinene (i.e., α-selinene, β-selinene, or mixtures thereof), eremophilene, nootkatene, or valencene; alternatively, farnesene; alternatively, bisabolene; alternatively, zingiberene; alternatively, β-curcumene; alternatively, laurene; alternatively, elemene; alternatively, humulene; alternatively, germacrene; alternatively, cadinene; alternatively, selinene; alternatively, eremophilene; alternatively, nootkatene; or alternatively, valencene.

In accordance with another embodiment, the compound can comprise, consist essentially of, or consist of, either singly or in any combination, cembrene, abietadiene, casbene, haslene, or squalene. Thus, each of these materials can be employed singularly; for example, the compound can comprise, consist essentially of, or consist of, haslene; alternatively, the compound having two or more double bonds can comprise, consist essentially of, or consist of, squalene.

In some embodiments, the compound can comprise, consist essentially of, or consist of, an unsaturated triglyceride, while in other embodiments, the compound can comprise, consist essentially of, or consist of, an unsaturated natural source oil. In an embodiment, the compound can comprise, consist essentially of, or consist of, either singly or in any combination, soybean oil, corn oil, castor bean oil, or canola oil. Such materials are disclosed, for instance, in U.S. Pat. No. 7,989,655, the disclosure of which is incorporated herein by reference in its entirety.

In yet another embodiment, the compound can comprise, consist essentially of, or consist of, either singly or in any combination, trisallyl isocyanurate, triallyl pentaerythritol, or trimethylolpropane diallylether.

Mercaptan Compounds

A mercaptan compound is a compound having at least one —SH group. Generally, the mercaptan compound can be any mercaptan compound which can be converted to a sulfide compound utilizing a process and/or flow reactor vessel described herein. Generally, the mercaptan compound can have any combination of the features for the mercaptan compound described herein. The mercaptan compound used in these processes has at least one SH group. In one embodiment, the mercaptan compound can have from 1 to 10 SH groups; alternatively, from 2 to 8 SH groups; alternatively, from 2 to 6 SH groups; or alternatively, from 1 to 4 SH groups. In another embodiment, the mercaptan compound has only one SH group; alternatively, only two SH groups; alternatively, only three SH groups; alternatively, only four SH groups; alternatively, only five SH groups; or alternatively, only six SH groups In an embodiment, the mercaptan compound used in the process can have at least 1 carbon atom, at least 2 carbon atoms, at least 3 carbon atoms, at 4 carbon atoms, or at least 5 carbon atoms. In some embodiments, the mercaptan compound used in the process can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the mercaptan compound used in the process can have from any minimum number of carbon atoms described herein to any maximum number of carbon atoms described herein. For example, in some non-limiting embodiments, the mercaptan compound can have from 1 to 100 carbon atoms, from 2 to 80 carbon atoms, from 1 to 60 carbon atoms, or from 2 to 60 carbon atoms. Other carbon atom number ranges can be readily envisioned from the present disclosure and are encompassed herein.

In an embodiment, the mercaptan compound can have the formula R—SH, the formula HS—R—SH, the formula HO—R—SH, or any combination thereof; alternatively R—SH; alternatively, HS—R—SH; or alternatively, HO—R—SH. In some embodiments, R can be a $C_1$-$C_{18}$ hydrocarbon group; alternatively, a $C_1$-$C_{10}$ hydrocarbon group; alternatively, a $C_1$-$C_5$ hydrocarbon group; alternatively, a $C_1$-$C_{18}$ alkane group; alternatively, a $C_1$-$C_{10}$ alkane group; alternatively, a $C_1$-$C_5$ alkane group; alternatively, a $C_1$-$C_{18}$ n-alkane group; alternatively, a $C_1$-$C_{10}$ n-alkane group; alternatively, a $C_1$-$C_5$ n-alkane group; alternatively, a $C_6$-$C_{18}$ arene group; alternatively, a $C_6$-$C_{10}$ arene group; alternatively, a $C_7$-$C_{18}$ alkylarene/arylalkane group; or alternatively, a $C_6$-$C_{10}$ alkylarene/arylalkane group. Accordingly, R can be a methane group, an ethane group, a propane group, a butane group, a pentane group, a hexane group, a heptane group, an octane group, a nonane group, or a decane group; alternatively, R can be a methane group, an ethane group, a propane group, a butane group, or a pentane group; alternatively, R can be a methane group; alternatively, R can be an ethane group; alternatively, R can be a propane group; alternatively, R can be a butane group; alternatively, R can be a pentane group; alternatively, R can be a hexane group; alternatively, R can be a heptane group; alternatively, R can be an octane group; alternatively, R can be a nonane group; or alternatively, R can be a decane group. In some embodiments, R can be a benzene group, a toluene group, a xylene group, or a naphthylene group; alternatively, a benzene group, a toluene group, or a xylene group; alternatively, a benzene group; alternatively, a toluene group; alternatively, a xylene group; or alternatively, a naphthylene group. In some embodiments, R can be a phenylalkane group or a naphthylalkane group; alternatively, a phenylalkane group; or alternatively, a naphthylalkane group. In further embodiments, R can be a phenylmethane group.

In accordance with an embodiment of this invention, the mercaptan compound can comprise, consist essentially of, or consist of, an alkyl mercaptan, for instance, an n-alkyl mercaptan. In accordance with another embodiment of this invention, the mercaptan compound can comprise, consist essentially of, or consist of, methyl mercaptan, ethyl mercaptan, n-propyl mercaptan, n-butyl mercaptan, t-butyl mercaptan, n-pentyl mercaptan, phenyl mercaptan, or combinations thereof. Yet, in accordance with another embodiment of this invention, the mercaptan compound can comprise, consist essentially of, or consist of, methyl mercaptan; alternatively, ethyl mercaptan; alternatively, n-propyl mercaptan; alternatively, n-butyl mercaptan; alternatively, t-butyl mercaptan; alternatively, n-pentyl mercaptan; or alternatively, phenyl mercaptan.

In some embodiments, the mercaptan compound can comprise, consist essentially of, or consist of, mercaptomethanol, 2-mercaptoethanol, 3-mercaptopropanol, 4-mercaptobutanol, 5-mercaptopentanol, 6-mercaptohexanol, or combinations thereof. In other embodiments, the mercaptan compound can comprise, consist essentially of, or consist of, mercaptomethanol; alternatively, 2-mercaptoethanol; alternatively, 3-mercaptopropanol; alternatively, 4-mercaptobutanol; alternatively, 5-mercaptopentanol; or alternatively, 6-mercaptohexanol. In yet another embodiment, the mercaptan compound can comprise, consist essentially of, or consist of, 1,2-dithioletane.

Phosphite Compounds

The phosphite compound, in certain embodiments, can comprise a compound having the formula:

$$P(OR^1)_3.$$

In this formula, each $R^1$ independently can be a $C_1$-$C_{18}$ hydrocarbyl group; alternatively, a $C_1$-$C_{10}$ hydrocarbyl group; alternatively, a $C_1$-$C_5$ hydrocarbyl group; alternatively, a $C_1$-$C_{18}$ alkyl group; alternatively, a $C_1$-$C_{10}$ alkyl group; alternatively, a $C_1$-$C_5$ alkyl group; alternatively, a $C_6$-$C_{18}$ aryl group; alternatively, a $C_6$-$C_{10}$ aryl group; alternatively, a $C_7$-$C_{18}$ alkylaryl/arylalkyl group; or alternatively, a $C_6$-$C_{10}$ alkylaryl/arylalkyl group. Accordingly, each $R^1$ independently can be a methyl group, an ethyl group, a propyl group, a butyl group, a pentyl group, a hexyl group, a heptyl group, an octyl group, a nonyl group, a decyl group; a propenyl group, a butenyl group, a pentenyl group, a hexenyl group, a heptenyl group, or a octenyl group; alternatively, $R^1$ can be a methyl group, an ethyl group, a propyl group, a butyl group, a pentyl group, a propenyl group, a butenyl group, or a pentenyl group; alternatively, $R^1$ can be a methyl group; alternatively, $R^1$ can be an ethyl group; alternatively, $R^1$ can be a propyl group; alternatively, $R^1$ can be a butyl group; alternatively, $R^1$ can be a pentyl group; alternatively, $R^1$ can be a hexyl group; alternatively, $R^1$ can be a heptyl group; alternatively, $R^1$ can be an octyl group; alternatively, $R^1$ can be a nonyl group; or alternatively, $R^1$ can be a decyl group. In some embodiments, each $R^1$ independently can be a phenyl group, a tolyl group, a xylyl group, or a naphthyl group; alternatively, a phenyl group, a tolyl group, or a xylyl group; alternatively, a phenyl group; alternatively, a tolyl group; alternatively, a xylyl group; or alternatively, a naphthyl group. In some embodiments, each $R^1$ independently can be a phenylalkyl group or a naphthylalkyl group; alternatively, a phenylalkyl group; or alternatively, a naphthylalkyl group. In further embodiments, $R^1$ can be a benzyl group.

In accordance with an embodiment of this invention, the phosphite compound can comprise, consist essentially of, or consist of, a trialkylphosphite, or alternatively, a triarylphosphite. In accordance with another embodiment of this invention, the phosphite compound can comprise, consist essentially of, or consist of, trimethylphosphite, triethylphosphite, tributylphosphite, or combinations thereof. Yet, in accordance with another embodiment of this invention, the phosphite compound can comprise, consist essentially of, or consist of, trimethylphosphite; alternatively, triethylphosphite; or alternatively, tributylphosphite. In another embodiment, the phosphite compound can comprise, consist essentially of, or consist of, triphenylphosphite.

Organic Reaction Medium

As described hereinabove, the fluid entering the flow reactor vessel can contain an organic reaction medium, and a thiol compound and/or sulfide compound can be formed in the presence of an organic reaction medium. The organic reaction medium can comprise, consist essentially of, or consist of, a hydrocarbon, a ketone, an alcohol, an ether, or combinations thereof alternatively, a hydrocarbon; alternatively, a ketone; alternatively, an alcohol; or alternatively, an ether. In some embodiments, the hydrocarbon organic reaction medium can comprise, consist essentially of, or consist of, an aliphatic hydrocarbon, an aromatic hydrocarbon, or combinations thereof alternatively, an aliphatic hydrocarbon; or alternatively, an aromatic hydrocarbon. In some embodiments, the organic reaction medium can be a non-olefinic organic reaction medium. Mixtures and/or combinations of the organic reaction medium can be utilized in the processes disclosed herein.

In an embodiment, the organic reaction medium can comprise, consist essentially of, or consist of, a hydrocarbon. Suitable hydrocarbons can include, for example, aliphatic hydrocarbons, petroleum distillates, or combinations thereof. Aliphatic hydrocarbons which can be useful as the organic reaction medium include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic, and/or can be linear or branched, unless otherwise specified. In some embodiments, the hydrocarbon organic medium can be non-olefinic.

Non-limiting examples of suitable acyclic aliphatic hydrocarbons that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, hexane (n-hexane or a mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

Non-limiting examples of suitable cyclic aliphatic hydrocarbons include, but are not limited to, cyclohexane, methyl cyclohexane, and the like, or combinations thereof alternatively, cyclohexane; or alternatively, methylcyclohexane.

In an embodiment, the organic reaction medium can comprise, consist essentially of, or consist of, an aromatic hydrocarbon. Aromatic hydrocarbons can include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof alternatively, benzene; alternatively, toluene; alternatively, xylene (including ortho-xylene, meta-xylene, para-xylene or mixtures thereof); or alternatively, ethylbenzene.

In an embodiment, a suitable organic reaction medium can comprise, consist essentially of, or consist of, a ketone, an alcohol, an ether, or combinations thereof alternatively, a ketone; alternatively, an alcohol; or alternatively, an ether. Such ketones, alcohols, or ethers include $C_2$ to $C_{20}$ ketones, alcohols, or ethers; alternatively, $C_2$ to $C_{10}$ ketones, alcohols, or ethers; or alternatively, $C_2$ to $C_5$ ketones, alcohols, or ethers. Non-limiting examples of suitable ketones can include acetone, ethyl methyl ketone, and combinations thereof. Non-limiting examples of suitable alcohols can include methanol, ethanol, propanol, isopropanol, n-butanol, isobutanol, pentanol, hexanol, heptanol, octanol, benzyl alcohol, phenol, cyclohexanol, and the like, or combinations thereof. Suitable ethers can be cyclic or acyclic, non-limiting examples of which can include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Examples 1-6

Mercaptanized Soybean Oil Experiments with a UV Flow Reactor Vessel

Examples 1-4 were performed using a 100-gallon flow reactor vessel system generally as described above and illustrated in FIG. 1 and FIGS. 2A-2B. The flow reactor vessel was equipped with a UV lamp, quartz tube, tube retainer, and a compression seal assembly, and a circulation pump was used to process the reaction fluid contained in a tank through the flow reactor vessel in a multi-pass operation. The outer reactor wall, in the longitudinal area where the UV lamp was positioned, was a nominal 3-inch pipe with an I.D. of about 2.9 inches. The quartz tube had an O.D. of about 2.3 inches and a nominal wall thickness of approximately 4 mm. The flow of the fluid in Examples 1-4 was turbulent flow; for instance, the Reynolds Number for Example 2 was 168,000. Comparative Example 5 used a 1,000-gallon continuous stirred tank reactor (CSTR) with 4 UV lamps, while Comparative Example 6 used a 500-gallon CSTR with 6 UV lamps. The wavelengths emitted by the respective medium pressure UV lamps useful for these experiments generally were in the 245-300 nm range. The efficiencies of the reactor systems of Examples 1-6 were compared during the production of mercaptanized soybean oil from a feed stream of soybean oil, $H_2S$ at a nominal 300:1 $H_2S$:soybean oil carbon-carbon double bond molar ratio (initial molar ratio), and tributylphosphite at 0.3 wt. % based on the weight of $H_2S$ (initial weight percentage). Reaction temperature was in the 25-45° C. range, reaction pressure was in the 250-450 psig range, and the pressure was controlled to maintain the $H_2S$ in the liquid phase. For these conditions and materials, the electromagnetic radiation penetration depth into the fluid in the flow path for Examples 1-4 was about 0.01 cm for photons in a 253-256 nm wavelength range.

Table I summarizes certain processing conditions and performance criteria for Examples 1-6. The circulation pump rate is listed in gallons per minute (GPM), the UV lamp power is listed in kilowatts (kW), the molar ratio is the initial $H_2S$:soybean oil double bond molar ratio, the production rate is the pounds of mercaptanized soybean oil produced per hour per number of UV lamps used (lb/hr/lamp), and the quantum yield is the moles of olefin carbon-carbon double bond reacted to form a SH group per mole of UV photons (for a reaction product having 9 wt. % SH). The quantum yield is a measure of the efficiency of using UV photons to affect a reaction between $H_2S$ and the soybean oil, with a higher number correlating with greater efficiency. The disappearance of the olefinic carbon-carbon double bonds in the soybean oil and the appearance of the carbon-sulfur bond were monitored via Raman Spectroscopy to determine the extent of conversion.

As shown in Table I, the UV flow reactor vessel and system used in Examples 1-4 was much more efficient than the CSTR and multiple lamp configuration used in Examples 5-6. Surprisingly, the average quantum yield of Examples 1-4 was 70% higher than the average quantum yield of Examples 5-6. Moreover, the production rates (in lb/hr/lamp) were higher for Examples 1-4, using the UV flow reactor vessel, than for Examples 5-6, using a CSTR configuration.

TABLE I

Examples 1-6.

| Example | Pump Rate (GPM) | UV Lamp (kW) | Molar Ratio | Production Rate (lb/hr/lamp) | Quantum Yield to 9 wt. % SH |
|---|---|---|---|---|---|
| 1 | 40 | 5 | 262 | 41.5 | 16.7 |
| 2 | 60 | 5 | 288 | 42.0 | 17.0 |
| 3 | 80 | 5 | 280 | 45.4 | 18.0 |
| 4 | 80 | 7.5 | 293 | 59.3 | 16.4 |
| 5 | N/A | 6 × 7.5 | 300 | 40.6 | 10.9 |
| 6 | N/A | 4 × 7.5 | 300 | 33.1 | 8.9 |

Examples 7-8

Production of n-Dodecyl-Mercaptan (NDDM) from 1-Dodecene with a UV Flow Reactor Vessel Example 7 was performed in substantially the same manner as in Examples 1-4, with the following exceptions. The initial charge of 1-dodecene was 92 lb, the initial charge of $H_2S$ was 420 lb (22.6:1 $H_2S$:carbon-carbon double bond molar ratio), and the initial charge of tributylphosphite was 600 g. The UV lamp wattage was 7.5 kW, and the pump circulation rate was 80 GPM. Reaction temperature was in the 25-45° C. range, reaction pressure was in the 250-450 psig range, and the pressure was controlled to maintain the $H_2S$ in the liquid phase. For these conditions and materials, the electromagnetic radiation penetration depth into the fluid in the flow path for Example 7 was about 0.012 cm for photons in a 253-256 nm wavelength range.

Figure 4:
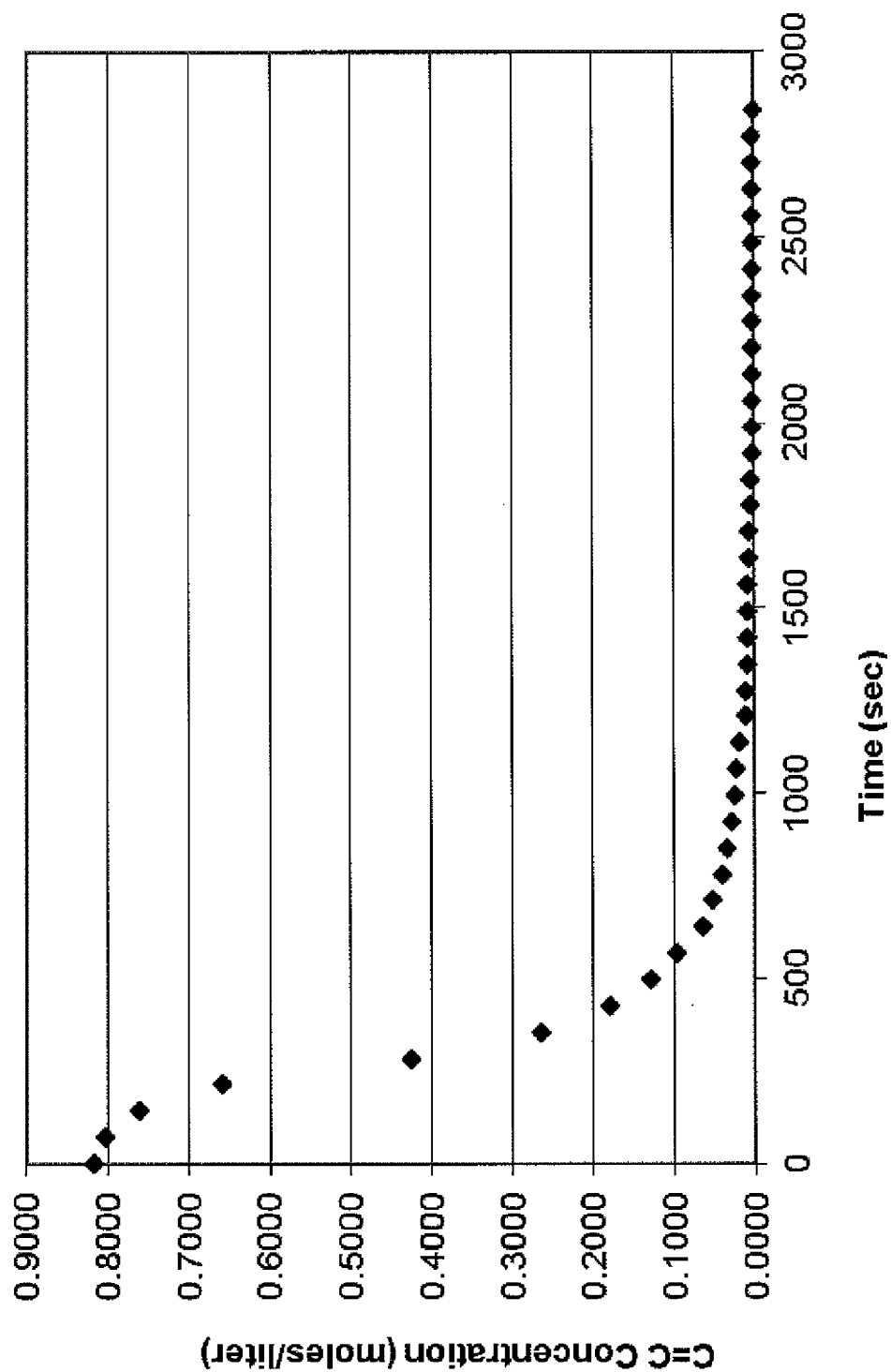
FIG. 4 presents a plot of the olefin concentration as a function of time for Example 7.
Figure 5:
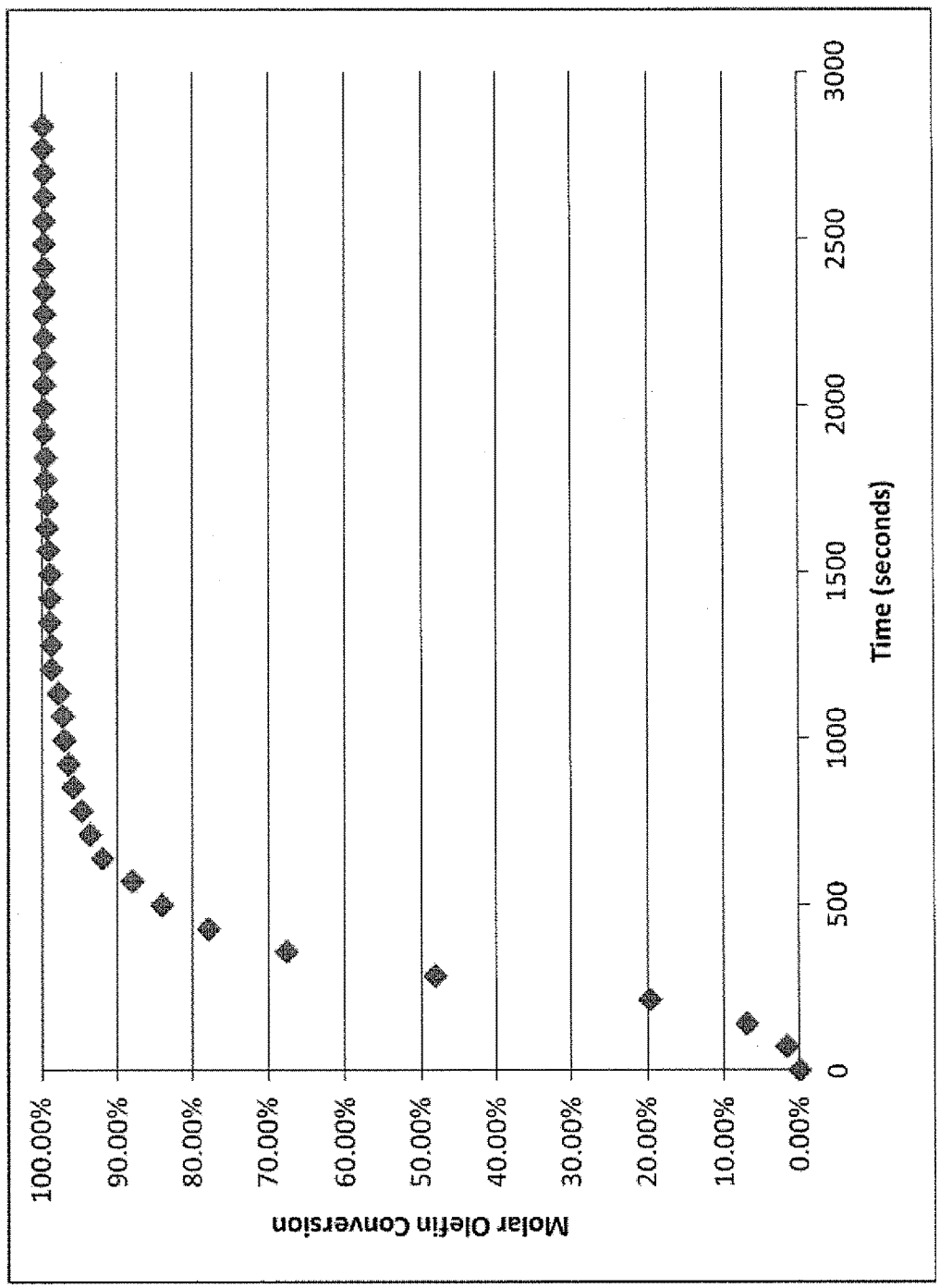
FIG. 5 presents a plot of the molar olefin conversion as a function of time for Example 7.

Using Raman Spectroscopy, the disappearance of olefinic carbon-carbon double bonds (1-dodecene) and the extent of olefin conversion were monitored. FIG. 4 illustrates the olefin concentration (in moles/liter) as a function of time, while FIG. 5 illustrates the molar olefin carbon-carbon double bond conversion to a carbon-sulfur bond as a function of time. The discontinuity in the first few samples was the result of lamp warm-up time; the lamp required approximately three minutes to reach full power. Using the UV flow reactor vessel, the molar olefin conversion reached 94% in about 12 minutes.

The quantum yield (moles of olefin carbon-carbon double bond reacted to form a SH group per mole of UV photons) to 94% molar olefin conversion for Example 7 was compared to that of Example 8, which used a reactor system consisting of three CSTR's in series. The system of Example 8 contained two 500-gallon CSTR's, each with 4 UV lamps (7.5 kW each), followed by one 1,000-gallon CSTR with 6 UV lamps (7.5 kW each).

The UV flow reactor vessel used in Example 7 was much more efficient than the series of CSTR's used in Example 8. The quantum yield for Example 8 was about 65, while the quantum yield for Example 7 was about 200. Notably, a 200% improvement in quantum yield resulted from using the UV flow reactor vessel.

Constructive Example 9

Constructive Reaction of 1-Octene and Ethyl Mercaptan in a UV Flow Reactor Vessel to form Ethyl n-Octyl Sulfide Constructive Example 9 can be performed in substantially the same manner as in Examples 1-8, with the following exceptions. The flow reactor system is a larger closed loop recirculation system containing 2 flow reactor vessels in series (each with a 7.5 kW UV lamp), followed by a heat exchanger, then 2 more flow reactor vessels in series (each with a 7.5 kW UV lamp), and a circulation pump capable of circulation rates in the 12-120 GPM range. The initial charge is 950 lb ethyl mercaptan and 1920 lb 1-octene having a nominal 98 wt. % purity (an approximate 1:1.1 SH:carbon-carbon double bond molar ratio). The reaction temperature is in the 15-90° C. range and controlled using the heat exchanger, and the reaction pressure is approximately 50 psig. For these conditions (e.g., circulation rate of 80 GPM and reaction temperature of 30° C.) and materials, the Reynolds Number for the fluid in the flow path of the flow reactor vessels is about 60,000.

Using Raman Spectroscopy, the disappearance of olefinic carbon-carbon double bonds (of 1-octene) and the extent of olefin conversion can be monitored. The flow reaction system can be operated, and the 1-octene and ethyl mercaptan reacted, for a time period of about one hour, which results in at least 99% molar conversion of SH (in ethyl mercaptan) to —S— (in ethyl n-octyl sulfide).

The invention has been described above with reference to numerous embodiments and specific examples. Many variations will suggest themselves to those skilled in the art in light of the above detailed description. All such obvious variations are within the full intended scope of the appended claims. Other embodiments of the invention can include, but are not limited to, the following:

Embodiment A. A flow reactor vessel comprising (a) a reaction chamber comprising a reactor wall, an inlet for a fluid, and an outlet; (b) a tube positioned within the reaction chamber, a flow path for the fluid including a region between an outer surface of the tube and an inner surface of the reactor wall; and (c) an electromagnetic radiation source enclosed within the tube, the electromagnetic radiation source configured to deliver radiation into the fluid in the flow path.

Embodiment B. The flow reactor vessel of embodiment A, wherein the tube is constructed of any material disclosed herein, e.g., quartz, Pyrex, a plastic, etc.

Embodiment C. The flow reactor vessel of embodiment A or B, wherein the tube is a quartz tube.

Embodiment D. The flow reactor vessel of any one of embodiments A to C, wherein the region between the outer surface of the tube and the inner surface of the reactor wall is an annular region.

Embodiment E. The flow reactor vessel of any one of embodiments A to D, wherein the average linear distance between the outer surface of the tube and the inner surface of the reactor wall is configured to be any factor of the electromagnetic radiation penetration depth into the fluid in the flow path disclosed herein, e.g., less than or equal to 1250 times, 1000 times, 750 times, 500 times, 400 times, 300 times, 200 times, 100 times, 50 times, 25 times, or 15 times the electromagnetic radiation penetration into the fluid in the flow path, or in a range from 1 to 1000 times, 30 to 500 times, 50 to 350 times, 30 to 400 times, 35 to 300 times, 1 to 75 times, 1.5 to 50 times, 2 to 30 times, or 2 to 15 times, etc., the electromagnetic radiation penetration depth into the fluid in the flow path.

Embodiment F. The flow reactor vessel of any one of embodiments A to E, wherein the average linear distance between the outer surface of the tube and the inner surface of the reactor wall is less than or equal to any linear distance or in any range of linear distances disclosed herein, e.g., a maximum value of 15 cm, 10 cm, 7 cm, 5 cm, 4 cm, 3 cm, 2.5 cm, 2 cm, 1.5 cm, or 1 cm, or in a range from 0.35 to 15 cm, from 0.4 to 10 cm, from 0.5 to 9 cm, from 0.6 cm to 8 cm, from 0.7 to 7 cm, from 0.5 cm to 3 cm, from 0.7 to 1.5 cm, from 1.5 to 5 cm, from 4 to 9 cm, from 4 to 6 cm, from 6 to 9 cm, etc.

Embodiment G. The flow reactor vessel of any one of embodiments A to F, wherein the ratio of the transverse cross-sectional area of the inner surface of the reactor wall to the outer surface of the tube is less than any maximum ratio disclosed herein, e.g., a maximum of 25:1, 15:1, 12:1, 7:1, 4:1, or 2:1, etc., or in any range of ratios disclosed herein, e.g., from 1.2:1 to 15:1, from 1.2:1 to 4:1, from 1.2:1 to 2:1, from 1.6:1 to 15:1, from 1.6:1 to 8:1, from 1.6:1 to 4.1, etc.

Embodiment H. The flow reactor vessel of any one of embodiments A to G, wherein the transverse cross-sectional area of the region between the outer surface of the tube and the inner surface of the reactor wall is less than or equal to any cross-sectional area disclosed herein, e.g., less than or equal to 750 cm$^2$, 500 cm$^2$, 300 cm$^2$, 100 cm$^2$, 60 cm$^2$, 25 cm$^2$, or 20 cm$^2$, etc., or in any range of cross-sectional areas disclosed herein, e.g., from 5 to 750 cm$^2$, from 10 to 400 cm$^2$, from 15 to 80 cm$^2$, from 15 to 60 cm$^2$, from 125 to 400 cm$^2$, from 10 to 100 cm$^2$, from 10 to 25 cm$^2$, etc.

Embodiment I. The flow reactor vessel of any one of embodiments A to H, wherein the tube has a minimum wall thickness of, e.g., 1 mm, 2 mm, 2.5 mm, 3 mm, 3.5 mm, 4 mm, 5 mm, etc., or alternatively, in any range of tube wall thicknesses disclosed herein, e.g., from 1 mm to 10 mm, from 2 mm to 5 mm, from 2.5 to 4.5 mm, etc.

Embodiment J. The flow reactor vessel of any one of embodiments A to I, wherein the flow reactor vessel and reaction chamber are configured for any operating pressure disclosed herein, e.g., a minimum pressure of at least 1.72 MPa, at least 2.41 MPa, at least 2.76 MPa, at least 3.45 MPa, or at least 4.14 MPa, etc.; or a maximum pressure of 13.79 MPa, 10.34 MPa, 6.89 MPa, 5.17 MPa, or 3.44 MPa, etc.; or a pressure in a range from 1.72 to 13.79 MPa, from 2.07 to 13.79 MPa, from 1.72 to 10.34 MPa, from 2.07 to 10.34 MPa, from 1.72 to 6.89 MPa, or from 2.07 to 5.17 MPa, etc.

Embodiment K. The flow reactor vessel of any one of embodiments A to I, wherein the flow reactor vessel and reaction chamber are configured for any operating pressure disclosed herein, e.g., a maximum pressure of 3.44 MPa, 1.72 MPa, 1.38 MPa, 1.03 MPa, 0.69 MPa, 0.52 MPa, or 0.34 MPa, etc.; or a minimum pressure of 0.10 MPa, 0.14 MPa, 0.17 MPa, or 0.34 MPa; or a pressure in a range from 0.1 to 3.44 MPa, from 0.14 to 1.38 MPa, from 0.14 to 1.03 MPa, from 0.14 to 0.69 MPa, from 0.14 to 0.52 MPa, or from 0.17 to 1.03 MPa , etc.

Embodiment L. The flow reactor vessel of any one of embodiments A to K, wherein the reaction chamber is configured to create turbulent flow in the flow path.

Embodiment M. The flow reactor vessel of any one of embodiments A to L, wherein the fluid in the flow path has turbulent flow and/or has any Reynolds number disclosed herein, e.g., at least 4,000, at least 5,000, at least 10,000, at least 50,000, from 4,000 to 300,000, from 5,000 to 200,000, etc.

Embodiment N. The flow reactor vessel of any one of embodiments A to M, wherein the reaction chamber further comprises any flow-affecting elements disclosed herein, e.g., baffles, in the flow path to promote turbulent flow.

Embodiment O. The flow reactor vessel of any one of embodiments A to N, wherein the radiation is any radiation disclosed herein, e.g., of radio waves, microwaves, infrared radiation, visible light, ultraviolet radiation, X-rays, gamma rays, etc., as well as combinations thereof.

Embodiment P. The flow reactor vessel of any one of embodiments A to O, wherein the electromagnetic radiation source is a ultraviolet light source capable of directing ultraviolet light at a wavelength in the 172 to 450 nm range, in the 185 to 380 nm range, in the 200 to 350 nm range, or in the 245 to 300 nm range, into the flow path.

Embodiment Q. The flow reactor vessel of any one of embodiments A to P, further comprising a compression seal assembly for sealing and securing the tube within the reaction chamber.

Embodiment R. The flow reactor vessel of embodiment Q, further comprising a tube retainer positioned on an opposite end of the reaction chamber from the compression seal assembly, the tube retainer configured to stabilize the tube, e.g., to prevent deflection.

Embodiment S. The flow reactor vessel of any one of embodiments A to R, further comprising an integrated heat exchange system around at least a portion of the reaction chamber for controlling temperature within the reaction chamber.

Embodiment T. The flow reactor vessel of embodiment S, wherein the heat exchange system surrounds the reaction chamber.

Embodiment U. The flow reactor vessel of any one of embodiments A to T, further comprising an inert gas delivery system for providing an inert atmosphere within the tube.

Embodiment V. The flow reactor vessel of any one of embodiments A to U, wherein the flow reactor vessel is a flow reactor vessel configured for mercaptanizing an olefin, a flow reactor vessel configured for reacting an olefin with a mercaptan to form a sulfide, and/or a flow reactor vessel configured for reacting an olefin with $H_2S$ to form a sulfide.

Embodiment W. A flow reactor system comprising two or more of any one of the flow reactor vessels of embodiments A to V, configured in series, in parallel, or any combination thereof.

Embodiment X. The system of embodiment W, wherein the flow reactor system comprises a heat exchanger before and/or after each flow reactor vessel.

Embodiment Y. The system of embodiment W, wherein a portion of two or more flow reactor vessels are surrounded by a single heat exchanger.

Embodiment Z. The system of embodiment W, wherein two or more flow reactor vessels are surrounded by a single heat exchanger.

Embodiment AA. The system of any one of embodiments W to Z, wherein the flow reactor system comprises two or more flow reactor vessels in series.

Embodiment BB. The system of any one of embodiments W to AA, wherein the flow reactor system comprises a single pass through each flow reactor vessel.

Embodiment CC. The system of any one of embodiments W to AA, wherein the flow reactor system comprises more than one pass through each flow reactor vessel.

Embodiment DD. A process for forming a thiol compound, the process comprising (i) introducing a fluid comprising $H_2S$ and a compound having a carbon-carbon double bond (i.e., at least one) into the inlet and the flow path of the flow reactor vessel of any one of embodiments A to V, or the flow reactor system of any one of embodiments W to CC; (ii) exposing the fluid to electromagnetic radiation within the reaction chamber to form a thiol compound; and (iii) discharging a composition comprising the thiol compound from the reaction chamber via the outlet.

Embodiment EE. The process of embodiment DD, wherein the pressure in the reaction chamber is any pressure sufficient to maintain $H_2S$ in the liquid phase during the exposing step.

Embodiment FF. The process of embodiment DD or EE, wherein the fluid in step (i) comprises a molar ratio of $H_2S$ to carbon-carbon double bonds of the compound having a carbon-carbon double bond in any range of molar ratios of $H_2S$ to carbon-carbon double bonds disclosed herein, e.g., from 5:1 to 500:1, from 15:1 to 150:1, from 20:1 to 75:1; from 20:1 to 50:1, etc.

Embodiment GG. A process for forming a sulfide compound, the process comprising (i) introducing a fluid comprising a mercaptan compound and a compound having a carbon-carbon double bond (i.e., at least one) into the inlet and the flow path of the flow reactor vessel of any one of embodiments A to V, or the flow reactor system of any one of embodiments W to CC; (ii) exposing the fluid to electromagnetic radiation within the reaction chamber to form a sulfide compound; and (iii) discharging a composition comprising the sulfide compound from the reaction chamber via the outlet.

Embodiment HH. The process of embodiment GG, wherein the fluid in step (i) comprises a molar ratio of SH of the mercaptan compound to carbon-carbon double bonds of the compound having a carbon-carbon double bond in any range of molar ratios of SH to carbon-carbon double bonds disclosed herein, e.g., from 10:1 to 1:10, from 2:1 to 1:2, from 1.5:1 to 1:1.5; from 1.1:1 to 1:1.1, etc.

Embodiment II. The process of any one of embodiments DD to HH, wherein the exposing step is conducted at any pressure disclosed herein, e.g., in the range from 1.72 MPa to 6.89 MPa, from 2.07 MPa to 5.17 MPa, from 0.14 to 0.90 MPa, from 0.14 to 0.75 MPa, etc.

Embodiment JJ. The process of any one of embodiments DD to II, wherein the exposing step is conducted at any temperature disclosed herein, e.g., at least 10° C., at least 20° C., at least 25° C., at least 30° C., in a range from 0° C. to 150° C., in a range from 15° C. to 100 ° C., in a range from 25° C. to 100° C., in a range from 20° C. to 80° C., etc.

Embodiment KK. The process of any one of embodiments DD to JJ, wherein the flow of the fluid in the flow path is turbulent flow and/or has any Reynolds number disclosed herein, e.g., at least 4,000, at least 5,000, at least 10,000, at least 50,000, from 4,000 to 300,000, from 5,000 to 200,000, etc.

Embodiment LL. The process of any one of embodiments DD to KK, wherein the fluid in step (i) further comprises a phosphite compound at an amount within any range of molar ratios of the phosphite compound to carbon-carbon double bonds disclosed herein, e.g., from 0.0005:1 to 0.10:1, from 0.006:1 to 0.05:1, etc.

Embodiment MM. The process of embodiment LL, wherein the phosphite compound is any phosphite compound disclosed herein, e.g., trimethylphosphite, triethylphosphite, tributylphosphite, etc., as well as combinations thereof.

Embodiment NN. The process of any one of embodiments DD to MM, wherein the fluid in step (i) further comprises any organic reaction medium disclosed herein, e.g., a hydrocarbon, a non-olefinic hydrocarbon, a ketone, an alcohol, an ether, etc., as well as combinations thereof.

Embodiment OO. The process of any one of embodiments DD to NN, wherein the fluid in step (i) further comprises any free radical initiator disclosed herein at an amount within any weight percentage range disclosed herein, e.g., from 0.1 to 9 wt. %, from 0.1 to 2 wt. %, etc.

Embodiment PP. The process of embodiment OO, wherein the exposing step is conducted at conditions suitable for the thermal decomposition of the free radical initiator.

Embodiment QQ. The process of any one of embodiments DD to PP, wherein the electromagnetic radiation is ultraviolet light.

Embodiment RR. The process of any one of embodiments DD to QQ, wherein the fluid in step (i) comprises any photoinitiator disclosed herein at an amount within any weight percentage range disclosed herein, e.g., from 0.05 to 5 wt. %, from 0.5 to 3 wt. %, etc.

Embodiment SS. The process of any one of embodiments DD to RR, wherein the compound having a carbon-carbon double bond has any number of carbon atoms disclosed herein (e.g., at least 3 carbon atoms, at least 4 carbon atoms, at least 5 carbon atoms, etc.), or any range of carbon atoms disclosed herein (e.g., from 2 to 100 carbon atoms, from 3 to 80 carbon atoms, from 4 to 60 carbon atoms, from 5 to 60 carbon atoms, etc.).

Embodiment TT. The process of any one of embodiments DD to RR, wherein the compound having a carbon-carbon double bond comprises ethylene, propylene, 1-butene, 2-butene, 3-methyl-1-butene, isobutylene, 1-pentene, 2-pentene, 3-methyl-l-pentene, 4-methyl-1-pentene, 1-hexene, 2-hexene, 3-ethyl-1-hexene, 1-heptene, 2-heptene, 3-heptene, 1-octene, 1-decene, 1-dodecene, styrene, or any combination thereof.

Embodiment UU. The process of any one of embodiments DD to RR, wherein the compound having a carbon-carbon double bond comprises cyclopentene, cyclohexene, cycloheptene, cyclooctene, or any combination thereof.

Embodiment VV. The process of any one of embodiments DD to RR, wherein the compound having a carbon-carbon double bond has at least two carbon-carbon double bonds.

Embodiment WW. The process of any one of embodiments DD to RR, wherein the compound having a carbon-carbon double bond comprises butadiene, isoprene, cyclobutadiene, cyclopentadiene, cyclohexadiene, cyclooctadiene, norbornadiene, vinylcyclohexene, vinylnorbomene, divinylbenzene, cyclopentadiene dimer, trivinylcyclohexane, trivinylbenzene, cycloheptatriene, dimethyl heptatriene, octatriene, cyclooctatriene, cyclododecatriene, cyclooctatetraene, cyclododecatetraene, a polybutadiene, or any combination thereof.

Embodiment XX. The process of any one of embodiments DD to RR, wherein the compound having a carbon-carbon double bond comprises an unsaturated triglyceride.

Embodiment YY. The process of any one of embodiments DD to RR, wherein the compound having a carbon-carbon double bond comprises an unsaturated natural source oil, e.g., soybean oil, corn oil, castor bean oil, canola oil, etc., as well as combinations thereof.

Embodiment ZZ. The process of any one of embodiments DD to RR, wherein the compound having a carbon-carbon double bond comprises D-limonene, alpha-pinene, or a combination thereof.

Embodiment AAA. The process of any one of embodiments DD to RR, wherein the compound having a carbon-carbon double bond comprises trisallyl isocyanurate, triallyl pentaerythritol, trimethylolpropane diallylether, or a combination thereof.

Embodiment BBB. The process of any one of embodiments GG to AAA, wherein the mercaptan compound has any number of carbon atoms disclosed herein (e.g., at least 1 carbon atom, at least 2 carbon atoms, at least 3 carbon atoms, etc.), or any range of carbon atoms disclosed herein (e.g., from 1 to 100 carbon atoms, from 2 to 80 carbon atoms, from 1 to 60 carbon atoms, etc.).

Embodiment CCC. The process of any one of embodiments GG to BBB, wherein the mercaptan compound has a number of SH groups in any range of number of SH groups disclosed herein, e.g., from 1 to 10, from 2 to 8, from 1 to 4, etc.

Embodiment DDD. The process of any one of embodiments GG to CCC, wherein the mercaptan compound comprises any mercaptan compound disclosed herein.

Embodiment EEE. The process of any one of embodiments GG to DDD, wherein the mercaptan compound comprises methyl mercaptan, ethyl mercaptan, n-propyl mercaptan, n-butyl mercaptan, t-butyl mercaptan, n-pentyl mercaptan, phenyl mercaptan, or any combination thereof.

Embodiment FFF. The process of any one of embodiments GG to DDD, wherein the mercaptan compound comprises mercaptomethanol, 2-mercaptoethanol, 3-mercaptopropanol, 4-mercaptobutanol, 5-mercaptopentanol, 6-mercaptohexanol, or any combination thereof.

We claimed:

1. A process for forming a thiol compound, the process comprising:
   (i) introducing a fluid comprising $H_2S$ and a compound having a carbon-carbon double bond into a flow reactor vessel, the flow reactor vessel comprising:
      (a) a reaction chamber comprising a reactor wall, an inlet for the fluid, and an outlet;
      (b) a tube positioned within the reaction chamber, and a flow path for the fluid including a region between an outer surface of the tube and an inner surface of the reactor wall; and
      (c) an electromagnetic radiation source enclosed within the tube, the electromagnetic radiation source configured to deliver electromagnetic radiation into the fluid in the flow path;
      wherein an average linear distance between the outer surface of the tube and the inner surface of the reactor wall is less than or equal to 10 cm;
   (ii) exposing the fluid to the electromagnetic radiation within the reaction chamber to form the thiol compound; and
   (iii) discharging a composition comprising the thiol compound from the reaction chamber via the outlet;
   wherein the fluid in the flow path has a volumetric flow rate from 12 to 120 gallons/min and a Reynolds number from 10,000 to 250,000; and
   wherein step (ii) is conducted at a reaction pressure sufficient to maintain $H_2S$ in the liquid phase.

2. The process of claim 1, wherein the fluid in step (i) comprises a molar ratio of $H_2S$ to carbon-carbon double bonds of the compound having a carbon-carbon double bond in a range from 5:1 to 500:1.

3. The process of claim 1, wherein the fluid in step (i) further comprises a phosphite compound at a molar ratio of the phosphite compound to carbon-carbon double bonds of the compound having a carbon-carbon double bond in a range from 0.006:1 to 0.05:1.

4. The process of claim 1, wherein the fluid in step (i) further comprises a photoinitiator at a weight percentage in a range from 0.05 to 5 wt. %, based on the weight of the compound having a carbon-carbon double bond.

5. The process of claim 1, wherein:
   the electromagnetic radiation is ultraviolet light; and
   step (ii) is conducted at a reaction pressure in a range from 1.72 to 13.79 MPa.

6. The process of claim 1, wherein the compound having a carbon-carbon double bond has from 1 to 10 double bonds.

7. The process of claim 1, wherein the compound having a carbon-carbon double bond comprises ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-dodecene, styrene, or any combination thereof.

8. The process of claim 1, wherein the compound having a carbon-carbon double bond comprises an unsaturated triglyceride, an unsaturated natural source oil, or both.

9. The process of claim 1, wherein the average linear distance between the outer surface of the tube and the inner surface of the reactor wall is greater than 10 times the electromagnetic radiation penetration depth into the fluid in the flow path.

10. The process of claim 1, wherein the fluid is substantially free of an organic reaction medium.

11. The process of claim 1, wherein the tube is a quartz tube having a wall thickness from 3.5 mm to 10 mm.

12. A process for forming a thiol compound, the process comprising:
- (i) introducing a fluid comprising $H_2S$ and a compound having a carbon-carbon double bond into a flow reactor vessel, the flow reactor vessel comprising:
  - (a) a reaction chamber comprising a reactor wall, an inlet for the fluid, and an outlet;
  - (b) a tube positioned within the reaction chamber, and a flow path for the fluid including a region between an outer surface of the tube and an inner surface of the reactor wall; and
  - (c) an electromagnetic radiation source enclosed within the tube, the electromagnetic radiation source configured to deliver electromagnetic radiation into the fluid in the flow path;
  - wherein an average linear distance between the outer surface of the tube and the inner surface of the reactor wall is less than or equal to 10 cm;
- (ii) exposing the fluid to the electromagnetic radiation within the reaction chamber to form the thiol compound; and
- (iii) discharging a composition comprising the thiol compound from the reaction chamber via the outlet;
- wherein the fluid in the flow path has a volumetric flow rate from 12 to 120 gallons/min and a Reynolds number of at least 10,000.

13. The process of claim 12, wherein the fluid in the flow path has a Reynolds number of at least 25,000.

14. The process of claim 12, wherein the fluid in the flow path has a Reynolds number of at least 50,000.

15. The process of claim 12, wherein:
- the electromagnetic radiation is ultraviolet light; and
- the fluid makes more than one pass through the flow reactor vessel.

16. The process of claim 12, wherein:
- the Reynolds number is from 25,000 to 200,000;
- the electromagnetic radiation is ultraviolet light; and
- the compound having a carbon-carbon double bond has from 2 to 6 double bonds.

17. The process of claim 12, wherein the fluid in step (i) comprises a molar ratio of $H_2S$ to carbon-carbon double bonds of the compound having a carbon-carbon double bond in a range from 15:1 to 150:1.

18. The process of claim 12, wherein step (ii) is conducted at a reaction pressure in a range from 1.72 MPa to 13.79 MPa.

19. The process of claim 12, wherein the tube is a quartz tube having a wall thickness from 3.5 mm to 10 mm.

20. The process of claim 12, wherein the fluid in step (i) further comprises:
- a phosphite compound at a molar ratio of the phosphite compound to carbon-carbon double bonds of the compound having a carbon-carbon double bond in a range from 0.006:1 to 0.05:1; and/or
- a photoinitiator at a weight percentage in a range from 0.05 to 5 wt. %, based on the weight of the compound having a carbon-carbon double bond.

* * * * *